(12) United States Patent
Janda et al.

(10) Patent No.: US 9,695,222 B2
(45) Date of Patent: Jul. 4, 2017

(54) GHRELIN MIMETIC POLYPEPTIDE HAPTEN IMMUNOCONJUGATES HAVING IMPROVED SOLUBILITY AND IMMUNOGENICITY AND METHODS OF USE THEREOF

(75) Inventors: Kim D. Janda, La Jolla, CA (US); Alexander V. Mayorov, Perm (RU)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 13/984,230

(22) PCT Filed: Feb. 9, 2012

(86) PCT No.: PCT/US2012/000079
§ 371 (c)(1),
(2), (4) Date: Oct. 4, 2013

(87) PCT Pub. No.: WO2012/108960
PCT Pub. Date: Aug. 16, 2012

(65) Prior Publication Data
US 2014/0086949 A1    Mar. 27, 2014

Related U.S. Application Data

(60) Provisional application No. 61/462,912, filed on Feb. 9, 2011.

(51) Int. Cl.
*C07K 14/575* (2006.01)
*C07K 14/33* (2006.01)
*A61K 39/00* (2006.01)
*A61K 39/385* (2006.01)
*A61K 47/48* (2006.01)
*C07K 14/34* (2006.01)
*C07K 14/47* (2006.01)

(52) U.S. Cl.
CPC .......... *C07K 14/33* (2013.01); *A61K 39/0012* (2013.01); *A61K 39/385* (2013.01); *A61K 47/48415* (2013.01); *A61K 47/48553* (2013.01); *C07K 14/34* (2013.01); *C07K 14/47* (2013.01); *C07K 14/575* (2013.01); *C07K 14/5759* (2013.01); *A61K 2039/6031* (2013.01); *A61K 2039/627* (2013.01)

(58) Field of Classification Search
CPC . A61K 14/48553; C07K 14/47; C07K 14/475
See application file for complete search history.

(56) References Cited

U.S. PATENT DOCUMENTS

2010/0021487 A1*   1/2010   Zorrilla et al. ............ 424/185.1
2010/0330108 A1*  12/2010   Song et al. ................ 424/179.1

OTHER PUBLICATIONS

Ana Spec available Oct. 2010 (1 page).*
Creative PegWorks Catalog 2010 (1 page).*
Peg Amino acid—Google search on Sep. 8, 2016 (2 pages).*

* cited by examiner

*Primary Examiner* — Gyan Chandra
(74) *Attorney, Agent, or Firm* — Hugh Wang; Thomas Fitting

(57) ABSTRACT

Immunoconjugates for impeding weight gain and treating obesity in a subject are disclosed. The immunoconjugates comprise a ghrelin mimetic polypeptide hapten, a spacer moiety comprising one of more polyethylene glycol (PEG) units, and a protein carrier moiety. Immunoconjugates optionally include a conjugation moiety for conjugating the polypeptide hapten with a linker moiety or the protein carrier moiety and a linker moiety for conjugating the conjugation moiety with the protein carrier moiety.

21 Claims, 5 Drawing Sheets

SEQUENCE LISTING

```
<160> NUMBER OF SEQ ID NOS: 32

<210> SEQ ID NO 1
<211> LENGTH: 23
<212> TYPE: PRT
<213> ORGANISM: Artificial
<220> FEATURE:
<223> OTHER INFORMATION: Homo sapiens or Rattus Norvegicus
<220> FEATURE:
<221> NAME/KEY: MISC_FEATURE
<222> LOCATION: (6)..(6)
<223> OTHER INFORMATION: Xaa at position 6 is either Lys (K) or Arg (R).
<220> FEATURE:
<221> NAME/KEY: MISC_FEATURE
<222> LOCATION: (7)..(7)
<223> OTHER INFORMATION: Xaa at position 7 is either Ala (A) or Val (V).

<400> SEQUENCE: 1

Ser Pro Glu His Gln Xaa Xaa Gln Gln Arg Lys Glu Ser Lys Lys Pro
1               5                   10                  15

Pro Ala Lys Leu Gln Pro Arg
            20
```

```
<210> SEQ ID NO 2
<211> LENGTH: 5
<212> TYPE: PRT
<213> ORGANISM: Artificial
<220> FEATURE:
<223> OTHER INFORMATION: a synthetic sequence
<220> FEATURE:
<221> NAME/KEY: MISC_FEATURE
<222> LOCATION: (3)..(3)
<223> OTHER INFORMATION: Xaa at position 3 is a modified serine of
      formula (I).

<400> SEQUENCE: 2

Gly Ser Xaa Phe Leu
1               5

<210> SEQ ID NO 3
<211> LENGTH: 6
<212> TYPE: PRT
<213> ORGANISM: Artificial
<220> FEATURE:
<223> OTHER INFORMATION: a synthetic sequence
<220> FEATURE:
<221> NAME/KEY: MISC_FEATURE
<222> LOCATION: (3)..(3)
<223> OTHER INFORMATION: Xaa at position 3 is a modified serine of
      formula (I).

<400> SEQUENCE: 3

Gly Ser Xaa Phe Leu Ser
1               5

<210> SEQ ID NO 4
<211> LENGTH: 7
<212> TYPE: PRT
<213> ORGANISM: Artificial
<220> FEATURE:
<223> OTHER INFORMATION: a synthetic sequence
<220> FEATURE:
<221> NAME/KEY: MISC_FEATURE
<222> LOCATION: (3)..(3)
<223> OTHER INFORMATION: Xaa at position 3 is a modified serine of
      formula (I).

<400> SEQUENCE: 4

Gly Ser Xaa Phe Leu Ser Pro
1               5

<210> SEQ ID NO 5
<211> LENGTH: 8
<212> TYPE: PRT
<213> ORGANISM: Artificial
<220> FEATURE:
<223> OTHER INFORMATION: a synthetic sequence
<220> FEATURE:
<221> NAME/KEY: MISC_FEATURE
<222> LOCATION: (3)..(3)
<223> OTHER INFORMATION: Xaa at position 3 is a modified serine of
      formula (I).

<400> SEQUENCE: 5

Gly Ser Xaa Phe Leu Ser Pro Glu
1               5

<210> SEQ ID NO 6
<211> LENGTH: 9
<212> TYPE: PRT
<213> ORGANISM: Artificial
<220> FEATURE:
```

```
<223> OTHER INFORMATION: a synthetic sequence
<220> FEATURE:
<221> NAME/KEY: MISC_FEATURE
<222> LOCATION: (3)..(3)
<223> OTHER INFORMATION: Xaa at position 3 is a modified serine of
      formula (I).

<400> SEQUENCE: 6

Gly Ser Xaa Phe Leu Ser Pro Glu His
1               5

<210> SEQ ID NO 7
<211> LENGTH: 10
<212> TYPE: PRT
<213> ORGANISM: Artificial
<220> FEATURE:
<223> OTHER INFORMATION: a synthetic sequence
<220> FEATURE:
<221> NAME/KEY: MISC_FEATURE
<222> LOCATION: (3)..(3)
<223> OTHER INFORMATION: Xaa at position 3 is a modified serine of
      formula (I).

<400> SEQUENCE: 7

Gly Ser Xaa Phe Leu Ser Pro Glu His Gln
1               5                   10

<210> SEQ ID NO 8
<211> LENGTH: 11
<212> TYPE: PRT
<213> ORGANISM: Artificial
<220> FEATURE:
<223> OTHER INFORMATION: a synthetic sequence
<220> FEATURE:
<221> NAME/KEY: MISC_FEATURE
<222> LOCATION: (3)..(3)
<223> OTHER INFORMATION: Xaa at position 3 is a modified serine of
      formula (I).
<220> FEATURE:
<221> NAME/KEY: MISC_FEATURE
<222> LOCATION: (11)..(11)
<223> OTHER INFORMATION: Xaa at position 11 is either Lys (K) or
      Arg (R).

<400> SEQUENCE: 8

Gly Ser Xaa Phe Leu Ser Pro Glu His Gln Xaa
1               5                   10

<210> SEQ ID NO 9
<211> LENGTH: 12
<212> TYPE: PRT
<213> ORGANISM: Artificial
<220> FEATURE:
<223> OTHER INFORMATION: a synthetic sequence
<220> FEATURE:
<221> NAME/KEY: MISC_FEATURE,
<222> LOCATION: (3)..(3)
<223> OTHER INFORMATION: Xaa at position 3 is a modified serine of
      formula (I).
<220> FEATURE:
<221> NAME/KEY: MISC_FEATURE
<222> LOCATION: (11)..(11)
<223> OTHER INFORMATION: Xaa at position 11 is either Lys (K) or
      Arg (R).
<220> FEATURE:
<221> NAME/KEY: MISC_FEATURE
<222> LOCATION: (12)..(12)
<223> OTHER INFORMATION: Xaa at position 11 is either Ala (A) or
      Val (V).

<400> SEQUENCE: 9

Gly Ser Xaa Phe Leu Ser Pro Glu His Gln Xaa Xaa
```

<210> SEQ ID NO 10
<211> LENGTH: 13
<212> TYPE: PRT
<213> ORGANISM: Artificial
<220> FEATURE:
<223> OTHER INFORMATION: a synthetic sequence
<220> FEATURE:
<221> NAME/KEY: MISC_FEATURE
<222> LOCATION: (3)..(3)
<223> OTHER INFORMATION: Xaa at position 3 is a modified serine of
      formula (I).
<220> FEATURE:
<221> NAME/KEY: MISC_FEATURE
<222> LOCATION: (11)..(11)
<223> OTHER INFORMATION: Xaa at position 11 is either Lys (K) or
      Arg (R).
<220> FEATURE:
<221> NAME/KEY: MISC_FEATURE
<222> LOCATION: (12)..(12)
<223> OTHER INFORMATION: Xaa at position 12 is either Ala (A) or
      Val (V).

<400> SEQUENCE: 10

Gly Ser Xaa Phe Leu Ser Pro Glu His Gln Xaa Xaa Gln
1               5                   10

<210> SEQ ID NO 11
<211> LENGTH: 14
<212> TYPE: PRT
<213> ORGANISM: Artificial
<220> FEATURE:
<223> OTHER INFORMATION: a synthetic sequence
<220> FEATURE:
<221> NAME/KEY: MISC_FEATURE
<222> LOCATION: (3)..(3)
<223> OTHER INFORMATION: Xaa at position 3 is a modified serine of
      formula (I).
<220> FEATURE:
<221> NAME/KEY: MISC_FEATURE
<222> LOCATION: (11)..(11)
<223> OTHER INFORMATION: Xaa at position 11 is either Lys (K) or
      Arg (R).
<220> FEATURE:
<221> NAME/KEY: MISC_FEATURE
<222> LOCATION: (12)..(12)
<223> OTHER INFORMATION: Xaa at position 12 is either Ala (A) or
      Val (V).

<400> SEQUENCE: 11

Gly Ser Xaa Phe Leu Ser Pro Glu His Gln Xaa Xaa Gln Gln
1               5                   10

<210> SEQ ID NO 12
<211> LENGTH: 15
<212> TYPE: PRT
<213> ORGANISM: Artificial
<220> FEATURE:
<223> OTHER INFORMATION: a synthetic sequence
<220> FEATURE:
<221> NAME/KEY: MISC_FEATURE
<222> LOCATION: (3)..(3)
<223> OTHER INFORMATION: Xaa at position 3 is a modified serine of
      formula (I).
<220> FEATURE:
<221> NAME/KEY: MISC_FEATURE
<222> LOCATION: (11)..(11)
<223> OTHER INFORMATION: Xaa at position 11 is either Lys (K) or
      Arg (R).
<220> FEATURE:
<221> NAME/KEY: MISC_FEATURE
<222> LOCATION: (12)..(12)
<223> OTHER INFORMATION: Xaa at position 12 is either Ala (A) or Val (V).

<400> SEQUENCE: 12

Gly Ser Xaa Phe Leu Ser Pro Glu His Gln Xaa Xaa Gln Gln Arg
1               5                   10                  15

<210> SEQ ID NO 13
<211> LENGTH: 16
<212> TYPE: PRT
<213> ORGANISM: Artificial
<220> FEATURE:
<223> OTHER INFORMATION: a synthetic sequence
<220> FEATURE:
<221> NAME/KEY: MISC_FEATURE
<222> LOCATION: (3)..(3)
<223> OTHER INFORMATION: Xaa at position 3 is a modified serine of
      formula (I).
<220> FEATURE:
<221> NAME/KEY: MISC_FEATURE
<222> LOCATION: (11)..(11)
<223> OTHER INFORMATION: Xaa at position 11 is either Lys (K) or
      Arg (R).
<220> FEATURE:
<221> NAME/KEY: MISC_FEATURE
<222> LOCATION: (12)..(12)
<223> OTHER INFORMATION: Xaa at position 12 is either Ala (A) or
      Val (V).

<400> SEQUENCE: 13

Gly Ser Xaa Phe Leu Ser Pro Glu His Gln Xaa Xaa Gln Gln Arg Lys
1               5                   10                  15

<210> SEQ ID NO 14
<211> LENGTH: 17
<212> TYPE: PRT
<213> ORGANISM: Artificial
<220> FEATURE:
<223> OTHER INFORMATION: a synthetic sequence
<220> FEATURE:
<221> NAME/KEY: MISC_FEATURE
<222> LOCATION: (3)..(3)
<223> OTHER INFORMATION: Xaa at position 3 is a modified serine of
      formula (I).
<220> FEATURE:
<221> NAME/KEY: MISC_FEATURE
<222> LOCATION: (11)..(11)
<223> OTHER INFORMATION: Xaa at position 11 is selected from Lys (K) or
      Arg (R).
<220> FEATURE:
<221> NAME/KEY: MISC_FEATURE
<222> LOCATION: (12)..(12)
<223> OTHER INFORMATION: Xaa at position 12 is selected from Ala (A) or
      Val (V).

<400> SEQUENCE: 14

Gly Ser Xaa Phe Leu Ser Pro Glu His Gln Xaa Xaa Gln Gln Arg Lys
1               5                   10                  15

Glu

<210> SEQ ID NO 15
<211> LENGTH: 18
<212> TYPE: PRT
<213> ORGANISM: Artificial
<220> FEATURE:
<223> OTHER INFORMATION: a synthetic sequence
<220> FEATURE:
<221> NAME/KEY: MISC_FEATURE
<222> LOCATION: (3)..(3)
<223> OTHER INFORMATION: Xaa at position 3 is a modified serine of
      formula (I).
<220> FEATURE:
<221> NAME/KEY: MISC_FEATURE

```
<222> LOCATION: (11)..(11)
<223> OTHER INFORMATION: Xaa at position 11 is either Lys (K) or
      Arg (R).
<220> FEATURE:
<221> NAME/KEY: MISC_FEATURE
<222> LOCATION: (12)..(12)
<223> OTHER INFORMATION: Xaa at position 12 is either Ala (A) or
      Val (V).

<400> SEQUENCE: 15

Gly Ser Xaa Phe Leu Ser Pro Glu His Gln Xaa Xaa Gln Gln Arg Lys
1               5                   10                  15

Glu Ser

<210> SEQ ID NO 16
<211> LENGTH: 19
<212> TYPE: PRT
<213> ORGANISM: Artificial
<220> FEATURE:
<223> OTHER INFORMATION: a synthetic sequence
<220> FEATURE:
<221> NAME/KEY: MISC_FEATURE
<222> LOCATION: (3)..(3)
<223> OTHER INFORMATION: Xaa at position 3 is a modified serine of
      formula (I).
<220> FEATURE:
<221> NAME/KEY: MISC_FEATURE
<222> LOCATION: (11)..(11)
<223> OTHER INFORMATION: Xaa at position 11 is either Lys (K) or
      Arg (R).
<220> FEATURE:
<221> NAME/KEY: MISC_FEATURE
<222> LOCATION: (12)..(12)
<223> OTHER INFORMATION: Xaa at position 12 is either Ala (A) or
      Val (V).

<400> SEQUENCE: 16

Gly Ser Xaa Phe Leu Ser Pro Glu His Gln Xaa Xaa Gln Gln Arg Lys
1               5                   10                  15

Glu Ser Lys

<210> SEQ ID NO 17
<211> LENGTH: 20
<212> TYPE: PRT
<213> ORGANISM: Artificial
<220> FEATURE:
<223> OTHER INFORMATION: a synthetic sequence
<220> FEATURE:
<221> NAME/KEY: MISC_FEATURE
<222> LOCATION: (3)..(3)
<223> OTHER INFORMATION: Xaa at position 3 is a modified serine of
      formula (I).
<220> FEATURE:
<221> NAME/KEY: MISC_FEATURE
<222> LOCATION: (11)..(11)
<223> OTHER INFORMATION: Xaa at position 11 is either Lys (K) or
      Arg (R).
<220> FEATURE:
<221> NAME/KEY: MISC_FEATURE
<222> LOCATION: (12)..(12)
<223> OTHER INFORMATION: Xaa at position 12 is either Ala (A) or
      Val (V).

<400> SEQUENCE: 17

Gly Ser Xaa Phe Leu Ser Pro Glu His Gln Xaa Xaa Gln Gln Arg Lys
1               5                   10                  15

Glu Ser Lys Lys
            20

<210> SEQ ID NO 18
```

```
<211> LENGTH: 21
<212> TYPE: PRT
<213> ORGANISM: Artificial
<220> FEATURE:
<223> OTHER INFORMATION: a synthetic sequence
<220> FEATURE:
<221> NAME/KEY: MISC_FEATURE
<222> LOCATION: (3)..(3)
<223> OTHER INFORMATION: Xaa at position 3 is a modified serine of
      formula (I).
<220> FEATURE:
<221> NAME/KEY: MISC_FEATURE
<222> LOCATION: (11)..(11)
<223> OTHER INFORMATION: Xaa at position 11 is either Lys (K) or
      Arg (R).
<220> FEATURE:
<221> NAME/KEY: MISC_FEATURE
<222> LOCATION: (12)..(12)
<223> OTHER INFORMATION: Xaa at position 12 is either Ala (A) or
      Val (V).

<400> SEQUENCE: 18

Gly Ser Xaa Phe Leu Ser Pro Glu His Gln Xaa Xaa Gln Gln Arg Lys
1               5                   10                  15

Glu Ser Lys Lys Pro
            20

<210> SEQ ID NO 19
<211> LENGTH: 22
<212> TYPE: PRT
<213> ORGANISM: Artificial
<220> FEATURE:
<223> OTHER INFORMATION: a synthetic sequence
<220> FEATURE:
<221> NAME/KEY: MISC_FEATURE
<222> LOCATION: (3)..(3)
<223> OTHER INFORMATION: Xaa at position 3 is a modified serine of
      formula (I).
<220> FEATURE:
<221> NAME/KEY: MISC_FEATURE
<222> LOCATION: (11)..(11)
<223> OTHER INFORMATION: Xaa at position 11 is either Lys (K) or
      Arg (R).
<220> FEATURE:
<221> NAME/KEY: MISC_FEATURE
<222> LOCATION: (12)..(12)
<223> OTHER INFORMATION: Xaa at position 12 is either Ala (A) or
      Val (V).

<400> SEQUENCE: 19

Gly Ser Xaa Phe Leu Ser Pro Glu His Gln Xaa Xaa Gln Gln Arg Lys
1               5                   10                  15

Glu Ser Lys Lys Pro Pro
            20

<210> SEQ ID NO 20
<211> LENGTH: 23
<212> TYPE: PRT
<213> ORGANISM: Artificial
<220> FEATURE:
<223> OTHER INFORMATION: a synthetic sequence
<220> FEATURE:
<221> NAME/KEY: MISC_FEATURE
<222> LOCATION: (3)..(3)
<223> OTHER INFORMATION: Xaa at position 3 is a modified serine of
      formula (I).
<220> FEATURE:
<221> NAME/KEY: MISC_FEATURE
<222> LOCATION: (11)..(11)
<223> OTHER INFORMATION: Xaa at position 11 is either Lys (K) or
      Arg (R).
<220> FEATURE:
<221> NAME/KEY: MISC_FEATURE
```

```
<222> LOCATION: (12)..(12)
<223> OTHER INFORMATION: Xaa at position 12 is either Ala (A) or
      Val (V).

<400> SEQUENCE: 20

Gly Ser Xaa Phe Leu Ser Pro Glu His Gln Xaa Xaa Gln Gln Arg Lys
1               5                   10                  15

Glu Ser Lys Lys Pro Pro Ala
            20

<210> SEQ ID NO 21
<211> LENGTH: 24
<212> TYPE: PRT
<213> ORGANISM: Artificial
<220> FEATURE:
<223> OTHER INFORMATION: a synthetic sequence
<220> FEATURE:
<221> NAME/KEY: MISC_FEATURE
<222> LOCATION: (3)..(3)
<223> OTHER INFORMATION: Xaa at position 3 is a modified serine of
      formula (I).
<220> FEATURE:
<221> NAME/KEY: MISC_FEATURE
<222> LOCATION: (11)..(11)
<223> OTHER INFORMATION: Xaa at position 11 is either Lys (K) or
      Arg (R).
<220> FEATURE:
<221> NAME/KEY: MISC_FEATURE
<222> LOCATION: (12)..(12)
<223> OTHER INFORMATION: Xaa at position 12 is either Ala (A) or
      Val (V).

<400> SEQUENCE: 21

Gly Ser Xaa Phe Leu Ser Pro Glu His Gln Xaa Xaa Gln Gln Arg Lys
1               5                   10                  15

Glu Ser Lys Lys Pro Pro Ala Lys
            20

<210> SEQ ID NO 22
<211> LENGTH: 25
<212> TYPE: PRT
<213> ORGANISM: Artificial
<220> FEATURE:
<223> OTHER INFORMATION: a synthetic sequence
<220> FEATURE:
<221> NAME/KEY: MISC_FEATURE
<222> LOCATION: (3)..(3)
<223> OTHER INFORMATION: Xaa at position 3 is a modified serine of
      formula (I).
<220> FEATURE:
<221> NAME/KEY: MISC_FEATURE
<222> LOCATION: (11)..(11)
<223> OTHER INFORMATION: Xaa at position 11 is either Lys (K) or
      Arg (R).
<220> FEATURE:
<221> NAME/KEY: MISC_FEATURE
<222> LOCATION: (12)..(12)
<223> OTHER INFORMATION: Xaa at position 12 is either Ala (A) or
      Val (V).

<400> SEQUENCE: 22

Gly Ser Xaa Phe Leu Ser Pro Glu His Gln Xaa Xaa Gln Gln Arg Lys
1               5                   10                  15

Glu Ser Lys Lys Pro Pro Ala Lys Leu
            20                  25

<210> SEQ ID NO 23
<211> LENGTH: 26
<212> TYPE: PRT
<213> ORGANISM: Artificial
```

```
<220> FEATURE:
<223> OTHER INFORMATION: a synthetic sequence
<220> FEATURE:
<221> NAME/KEY: MISC_FEATURE
<222> LOCATION: (3)..(3)
<223> OTHER INFORMATION: Xaa at position 3 is a modified serine of
      formula (I).
<220> FEATURE:
<221> NAME/KEY: MISC_FEATURE
<222> LOCATION: (11)..(11)
<223> OTHER INFORMATION: Xaa at position 11 is either Lys (K) or
      Arg (R).
<220> FEATURE:
<221> NAME/KEY: MISC_FEATURE
<222> LOCATION: (12)..(12)
<223> OTHER INFORMATION: Xaa at position 12 is either Ala (A) or
      Val (V).

<400> SEQUENCE: 23

Gly Ser Xaa Phe Leu Ser Pro Glu His Gln Xaa Xaa Gln Gln Arg Lys
1               5                   10                  15

Glu Ser Lys Lys Pro Pro Ala Lys Leu Gln
            20                  25

<210> SEQ ID NO 24
<211> LENGTH: 27
<212> TYPE: PRT
<213> ORGANISM: Artificial
<220> FEATURE:
<223> OTHER INFORMATION: a synthetic sequence
<220> FEATURE:
<221> NAME/KEY: MISC_FEATURE
<222> LOCATION: (3)..(3)
<223> OTHER INFORMATION: Xaa at position 3 is a modified serine of
      formula (I).
<220> FEATURE:
<221> NAME/KEY: MISC_FEATURE
<222> LOCATION: (11)..(11)
<223> OTHER INFORMATION: Xaa at position 11 is either Lys (K) or
      Arg (R).
<220> FEATURE:
<221> NAME/KEY: MISC_FEATURE
<222> LOCATION: (12)..(12)
<223> OTHER INFORMATION: Xaa at position 12 is either Ala (A) or
      Val (V).

<400> SEQUENCE: 24

Gly Ser Xaa Phe Leu Ser Pro Glu His Gln Xaa Xaa Gln Gln Arg Lys
1               5                   10                  15

Glu Ser Lys Lys Pro Pro Ala Lys Leu Gln Pro
            20                  25

<210> SEQ ID NO 25
<211> LENGTH: 28
<212> TYPE: PRT
<213> ORGANISM: Artificial
<220> FEATURE:
<223> OTHER INFORMATION: a synthetic sequence
<220> FEATURE:
<221> NAME/KEY: MISC_FEATURE
<222> LOCATION: (3)..(3)
<223> OTHER INFORMATION: Xaa at position 3 is a modified serine of
      formula (I).
<220> FEATURE:
<221> NAME/KEY: MISC_FEATURE
<222> LOCATION: (11)..(11)
<223> OTHER INFORMATION: Xaa at position 11 is either Lys (K) or
      Arg (R).
<220> FEATURE:
<221> NAME/KEY: MISC_FEATURE
<222> LOCATION: (12)..(12)
<223> OTHER INFORMATION: Xaa at position 12 is either Ala (A) or
      Val (V).
```

```
<400> SEQUENCE: 25

Gly Ser Xaa Phe Leu Ser Pro Glu His Gln Xaa Xaa Gln Gln Arg Lys
1               5                   10                  15

Glu Ser Lys Lys Pro Pro Ala Lys Leu Gln Pro Arg
            20                  25

<210> SEQ ID NO 26
<211> LENGTH: 11
<212> TYPE: PRT
<213> ORGANISM: Artificial
<220> FEATURE:
<223> OTHER INFORMATION: a synthetic sequence
<220> FEATURE:
<221> NAME/KEY: MISC_FEATURE
<222> LOCATION: (3)..(3)
<223> OTHER INFORMATION: Xaa at position 3 is a modified serine of
      formula (I), butyryl serine.

<400> SEQUENCE: 26

Gly Ser Xaa Phe Leu Ser Pro Glu His Gln Cys
1               5                   10

<210> SEQ ID NO 27
<211> LENGTH: 17
<212> TYPE: PRT
<213> ORGANISM: Artificial
<220> FEATURE:
<223> OTHER INFORMATION: Homo sapiens or Rattus Norvegicus

<400> SEQUENCE: 27

Cys Gln Gln Arg Lys Glu Ser Lys Lys Pro Pro Ala Lys Leu Gln Pro Arg
1               5                   10                  15

<210> SEQ ID NO 28
<211> LENGTH: 29
<212> TYPE: PRT
<213> ORGANISM: Artificial
<220> FEATURE:
<221> NAME/KEY: MISC_FEATURE,
<222> LOCATION: (3)..(3)
<223> OTHER INFORMATION: Xaa at position 3 is a modified serine of
      formula (I), butyryl serine.

<400> SEQUENCE: 28

Gly Ser Xaa Phe Leu Ser Pro Glu His Gln Lys Ala Gln Gln Arg Lys Glu
1               5                   10                  15

Ser Lys Lys Pro Pro Ala Lys Leu Gln Pro Arg Cys
            20                  25

<210> SEQ ID NO 29
<211> LENGTH: 6
<212> TYPE: PRT
<213> ORGANISM: Artificial
<220> FEATURE:
<223> OTHER INFORMATION: a synthetic sequence
<220> FEATURE:
<221> NAME/KEY: MISC_FEATURE
<222> LOCATION: (3)..(3)
<223> OTHER INFORMATION: Xaa at position 3 is a modified serine of
      formula (I), butyryl serine.

<400> SEQUENCE: 29

Gly Ser Xaa Phe Leu Cys
1               5

<210> SEQ ID NO 30
```

```
<211> LENGTH: 6
<212> TYPE: PRT
<213> ORGANISM: Artificial
<220> FEATURE:
<223> OTHER INFORMATION: a synthetic sequence
<220> FEATURE:
<221> NAME/KEY: MISC_FEATURE
<222> LOCATION: (3)..(3)
<223> OTHER INFORMATION: Xaa at position 3 is a modified serine of
      formula (I), octanoyl serine.

<400> SEQUENCE: 30

Gly Ser Xaa Phe Leu Cys
1               5

<210> SEQ ID NO 31
<211> LENGTH: 6
<212> TYPE: PRT
<213> ORGANISM: Artificial
<220> FEATURE:
<223> OTHER INFORMATION: a synthetic sequence
<220> FEATURE:
<221> NAME/KEY: MISC_FEATURE
<222> LOCATION: (3)..(3)
<223> OTHER INFORMATION: Xaa at position 3 is a modified serine of
      formula (I), butyryl serine.
<220> FEATURE:
<221> NAME/KEY: MISC_FEATURE
<222> LOCATION: (6)..(6)
<223> OTHER INFORMATION: Xaa at position 6 is a PEG4 modified cysteine.

<400> SEQUENCE: 31

Gly Ser Xaa Phe Leu Xaa
1               5

<210> SEQ ID NO 32
<211> LENGTH: 6
<212> TYPE: PRT
<213> ORGANISM: Artificial
<220> FEATURE:
<223> OTHER INFORMATION: a synthetic sequence
<220> FEATURE:
<221> NAME/KEY: MISC_FEATURE
<222> LOCATION: (3)..(3)
<223> OTHER INFORMATION: Xaa at position 3 is a modified serine of
      formula (I), octanoyl serine.
<220> FEATURE:
<221> NAME/KEY: MISC_FEATURE
<222> LOCATION: (6)..(6)
<223> OTHER INFORMATION: Xaa at position 6 is a PEG4 modified cysteine.

<400> SEQUENCE: 32

Gly Ser Xaa Phe Leu Xaa
1               5
```

GHRELIN MIMETIC POLYPEPTIDE HAPTEN IMMUNOCONJUGATES HAVING IMPROVED SOLUBILITY AND IMMUNOGENICITY AND METHODS OF USE THEREOF

CROSS-REFERENCE TO RELATED APPLICATIONS

The subject patent application claims the benefit of priority to U.S. Provisional Patent Application No. 61/462,912 (filed Feb. 9, 2011). The full disclosure of the priority application is incorporated herein by reference in its entirety and for all purposes.

BACKGROUND

Obesity endangers the lives of millions of people worldwide, through comorbidities such as heart disease, cancers, type 2 diabetes, stroke, arthritis, and major depression. At this time, available non-surgical treatments for obesity, including drugs, are palliative and effective only while treatment is maintained. When treatments are discontinued, weight gain inevitably results. For obesity treatments to work, they must affect energy intake, absorption, expenditure or storage. While many drugs have been marketed or are currently under investigation for the treatment of obesity, several have adverse side effects, including insomnia, asthenia, fecal incontinence, hypertension, tachychardia, valvular heart abnormalities, and even death. Accordingly, several weight loss drugs have been banned by the Food and Drug Administration, including the first one approved for this indication, desoxyephedrine (1946), and more recently d-fenfluramine/fenfluramine (September, 1997) and ephedrine alkaloids (April, 2004).

Research over the past fifteen years has revolutionized the understanding of molecular mechanisms that homeostatically control body weight and fat. Accumulated findings support a lipostatic hypothesis of energy homeostasis, in which the brain seeks to retain stored energy constant over long periods as adipose tissue. Accordingly, a highly integrated, redundant neurohumoral energy homeostasis feedback system, through behavioral and metabolic mechanisms, serves to minimize the impact of short-term fluctuations in energy balance, and especially negative energy balance, on fat mass. The identification of genes whose loss of function mutations result in monogenic obesity syndromes or confer resistance to obesity in humans or rodents have provided critical genetic entry points for characterizing the interconnected pathways that regulate energy homeostasis. The identification of these receptors and ligands has led to research efforts to target signals at both ends of the energy spectrum, however, no vaccine or treatment modality based on these research efforts is currently available for treating obese patients.

SUMMARY OF THE INVENTION

The inventors have discovered that the bioavailability of the gastric endocrine hormone ghrelin via active immunization with ghrelin-derived polypeptide immunoconjugates is improved by increasing the solubility and immunogenicity of the polypeptide through the use of a hydrophilic spacer comprising polyethylene glycol (PEG) units. Modulation of the bioavailability of ghrelin-derived polypeptide immunoconjugates provides means to regulate energy balance and slow weight gain while sparing lean mass.

Accordingly, in one aspect, the invention provides an immunoconjugate which comprises a ghrelin mimetic polypeptide hapten and a carrier moiety, wherein the polypeptide hapten is linked to the carrier moiety by a hydrophilic spacer moiety. The immunoconjugates of the invention comprise the following structure:

```
Gly-Ser-A-Phe-Leu-B-C-F;

Gly-Ser-A-Phe-Leu-B-C-D-F;
or

Gly-Ser-A-Phe-Leu-B-C-D-E-F
``` wherein A, B, C, D, E, and F are defined as follows:
A is a moiety having the following structure:

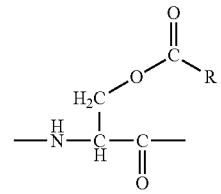

wherein: R is a saturated or unsaturated, branched or unbranched, substituted or unsubstituted hydrocarbon group having about 3 to about 10 carbon atoms, or is a cycloalkyl or aryl group having about 3 to about 13 carbon atoms;
B comprises a subsequence of 0 to 23 consecutive amino acid residues of SEQ ID NO: 1, which comprises the following sequence:

```
                                             (SEQ ID NO: 1)
Ser Pro Glu His Gln Lys/Arg Ala/Val Gln Gln Arg Lys

Glu Ser Lys Lys Pro Pro Ala Lys Leu Gln Pro Arg;
```

C comprises a spacer moiety comprising a sequence of 1 to about 5 consecutive PEG amino acid spacers (p) containing 1 to about 40 polyethylene glycol (PEG) units:

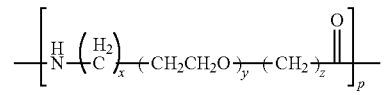

wherein x is between 0 and 1 inclusive, y is between 1 and 40 inclusive, z is between 1 and 3 inclusive, p is between 1 and 5 inclusive, and p*y is between 1 and 40 inclusive;
D comprises a conjugation moiety with chemical functionality suitable for conjugation with the linker moiety or directly with the carrier protein;
E comprises a linker moiety with chemical functionality suitable for conjugation with the conjugation moiety; and
F comprises a protein carrier moiety.

In another aspect, the invention provides a composition comprising an immunogenically effective amount of the immunoconjugate of the inventions and a physiologically acceptable vehicle. Preferably, the composition is an immunogenic composition, such as a vaccine composition.

In yet another aspect, the invention provides a method of inducing an anti-ghrelin immune response in a subject comprising administering to the subject a composition comprising an immunologically effective amount of an immunoconjugate of the invention and a physiologically acceptable vehicle.

In a further aspect, the invention provides a method of controlling adiposity in a subject. The method encompasses administering to the subject an immunoconjugate of the invention or a composition comprising an immunoconjugate of the invention.

BRIEF DESCRIPTION OF THE DRAWINGS

FIG. 4 is a graphical representation comparing the ghrelin hapten titers against BSA-acylated ghrelin in plasma collected from animals from the 2$^{nd}$, 3$^{rd}$, 4$^{th}$ and 5$^{th}$ bleeds after immunization with various ghrelin immunoconjugates.

FIG. 5 is a graphical representation of body composition at the 5$^{th}$ bleed in relation to anti-ghrelin affinity at the 5$^{th}$ bleed.

DESCRIPTION OF ILLUSTRATIVE EMBODIMENTS

Figure 1:
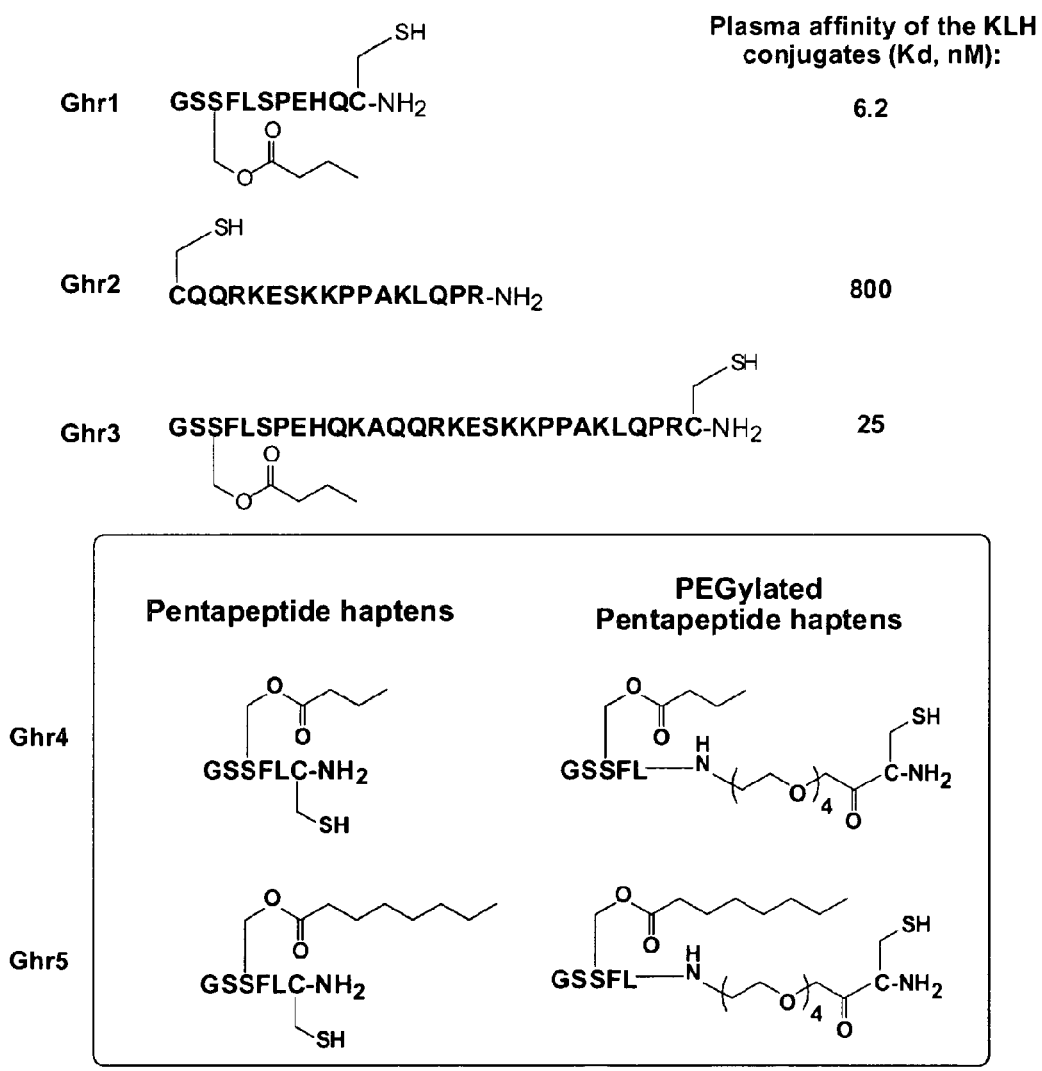
FIG. 1 shows the structures of several ghrelin-derived haptens and the corresponding immunoconjugates, Ghr1 (SEQ ID NO:26), Ghr2 (SEQ ID NO:27), Ghr3 (SEQ ID NO:28), Ghr4 (SEQ ID NO:29), pegylated Ghr4 (SEQ ID NO:31), Ghr5 (SEQ ID NO:30), and pegylated Ghr5 (SEQ ID NO:32).

Ghrelin is an endogenous ligand for the growth hormone secretagogue receptor (ghrelin receptor) localized to peripheral tissues and hypothalamic nuclei that control energy homeostasis. Studies have found a preprandial rise and a postprandial decline in plasma ghrelin levels of putative gastric origin, suggesting that ghrelin may play a role in energy homeostasis. Ghrelin is orexigenic when administered to humans or sated rodents with a central site of action. Ghrelin promotes weight gain and adiposity through metabolic action, decreasing both energy expenditure and fat catabolism. In longer term energy homeostasis, ghrelin levels are persistently increased during weight loss and suppressed in the obese state. Consistent with this role, mice deficient for ghrelin or its receptor store less of their consumed food and resist accumulating body weight and fat on energy-dense diets. Ghrelin knockout mice also expend more energy and locomote more, with ghrelin receptor deficient mice show increased whole-body fat oxidation.

Ghrelin is the first peptide isolated from animal sources with the posttranslational modification of octanoylation. Specifically, the hydroxyl group of a Ser residue (Ser-3) is acylated by n-octanoic acid. Octanoylation is essential for the growth hormone-releasing activity of ghrelin, and short peptides encompassing the first 4-5 residues of ghrelin activate the growth hormone secretagogue receptor as efficiently as full length ghrelin.

Ghrelin mimetic polypeptide hapten structures and immunoconjugates comprising the ghrelin mimetic polypeptide hapten structures are described in WO2008/016976, the entirety of which is herein incorporated by reference. The inventors have discovered that incorporation of a hydrophilic spacer moiety comprising a subsequence of 1 to about 5 consecutive PEG amino acid spacers containing one or more polyethylene glycol (PEG) units into ghrelin mimetic hapten structures markedly improves the solubility of the ghrelin mimetic haptens and corresponding immunoconjugates. Incorporation of the spacer moiety provided ghrelin mimetic haptens and corresponding immunoconjugates that were unexpectedly found to have enhanced immunogenicity and efficacy. The enhanced solubility and immunogenicity of the immunoconjugates of the invention simplify the formulation of immunogenic compositions, such as vaccines, comprising the immunoconjugates of the invention.

The present invention provides ghrelin mimetic polypeptide haptens and immunoconjugates thereof, wherein the hapten portion of the immunoconjugate includes a modified serine residue at the third amino acid position, and the immunoconjugate includes a hydrophilic spacer moiety, such as a PEG moiety for example, as described herein. The immunoconjugates are suitably represented by the following sequences:

```
Gly-Ser-A-Phe-Leu-B-C-F;

Gly-Ser-A-Phe-Leu-B-C-D-F;
or

Gly-Ser-A-Phe-Leu-B-C-D-E-F
``` wherein A, B, C, D, E and F are defined as follows:

A is a moiety having the following structure:

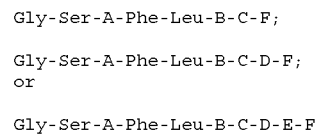

wherein: R is a saturated or unsaturated, branched or unbranched, substituted or unsubstituted hydrocarbon group having about 3 to about 10 carbon atoms, or is a cycloalkyl or aryl group having about 3 to about 13 carbon atoms;

B comprises a subsequence of 0 to 23 consecutive amino acid residues of SEQ ID NO: 1; which comprises the following sequence:

```
                                            (SEQ ID NO: 1)
Ser Pro Glu His Gln Lys/Arg Ala/Val Gln Gln Arg Lys

Glu Ser Lys Lys Pro Pro Ala Lys Leu Gln Pro Arg;
```

C comprises a spacer moiety comprising a sequence of 1 to about 5 consecutive PEG amino acid spacers (p) containing 1 to about 40 polyethylene glycol (PEG) units:

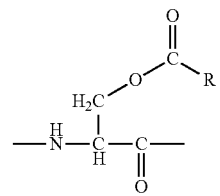

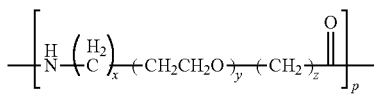

wherein x is between 0 and 1 inclusive, y is between 1 and 40 inclusive, z is between 1 and 3 inclusive, p is between 1 and 5 inclusive, and p*y is 40 or less;

D comprises a conjugation moiety with chemical functionality suitable for conjugation with the linker moiety or directly with the carrier protein;

E comprises a linker moiety with chemical functionality suitable for conjugation with the conjugation moiety; and F comprises a protein carrier moiety.

It has been found that a spacer moiety comprising polyethylene glycol (PEG) units markedly improves water-solubility of both the polypeptide haptens and the corresponding immunoconjugates with suitable protein carriers. The inclusion of the spacer moiety in the immunoconjugates increases the solubility of the haptens and immunoconjugates thereof, and surprisingly, also enhances the immunogenicity and efficacy of the respective immunoconjugates, even though the inclusion of PEG in polypeptide chains is known in the art to reduce immunogenicity. The increased solubility of the PEG-containing haptens simplifies formulation of immunogenic compositions, such as vaccines, based on such immunoconjugates. The immunoconjugates are suitably included in a vaccine composition with a physiologically acceptable vehicle. The invention also provides methods of inducing an anti-ghrelin immune response in a subject and controlling adiposity in a subject with the immunoconjugates of the invention Ghrelin Mimetic Polypeptide Haptens As used herein and in the art, the term "polypeptide" refers to two or more amino acid moieties linked by amide bonds, and includes both peptides and proteins. The polypeptide haptens of the invention may be purified or synthetic. "Purified" refers to material that is at least partially separated from components which normally accompany it in its native state. As is appreciated by skilled artisans, purity of polypeptides is typically determined using analytical techniques such as polyacrylamide gel electrophoresis or high performance liquid chromatography. As used herein, "synthetic" refers to both recombinantly produced and prepared via solid phase techniques, as known in the art. The term "hapten" refers to a low molecular weight substance such as a peptide, small protein or drug molecule that is generally not immunogenic and requires a carrier protein to stimulate an immunological response in a system.

Short peptides that encompass the first 4-5 residues of ghrelin activate the growth hormone secretagogue receptor as efficiently as full-length ghrelin, suggesting that the N-terminal Gly-Ser-Ser(n-octanoyl)-Phe segment constitutes the requisite core for receptor binding and activation. The polypeptides of the invention are "ghrelin mimetic polypeptides" or "ghrelin mimetic haptens" or "ghrelin mimetic polypeptide haptens" or "ghrelin haptens" and these terms are used interchangeably. The polypeptide constructs of the invention comprise, at minimum, a sequence of amino acids comprising Gly-Ser-A-Phe Leu (SEQ ID NO:2), wherein A denotes a modified serine residue having a structure of formula (I):

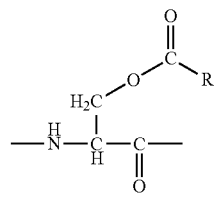

With reference to formula (I), R is a saturated or unsaturated, branched or unbranched, substituted or unsubstituted hydrocarbon group having about 3 to about 10 carbon atoms, or is a cycloalkyl or aryl group having about 3 to about 13 carbon atoms. As used herein, as "hydrocarbon group" refers to an aliphatic hydrocarbon group having a specified number of carbon atoms in the chain. The hydrocarbon group may comprise, e.g., an alkyl, an alkenyl or alkynyl group. In an embodiment, R comprises —CH$_2$CH$_2$CH$_3$. In another embodiment, R comprises —CH$_2$CH$_2$CH$_2$CH$_2$CH$_2$CH$_2$CH$_3$.

In an embodiment, the modified serine (A) is acylated. In an embodiment, the modified serine (A) is acylated by n-octanoic acid. In an embodiment, the modified serine (A) comprises a butanoyl ester.

The polypeptide constructs of the invention may further comprise Gly-Ser-A-Phe-Leu-B, where B is a carboxy-terminal subsequence of the full length ghrelin polypeptide. The subsequence includes any of SEQ ID NO:1 or the full sequence of SEQ ID NO:1. In other words, the ghrelin polypeptide comprises SEQ ID NO: 2 and a sequence or subsequence of SEQ ID NO: 1. For example, the ghrelin-derived polypeptide constructs of the invention can comprise any of the following sequences:

Gly Ser Xaa Phe Leu (SEQ ID NO:2);

```
                                          (SEQ ID NO: 1)
Gly Ser Xaa Phe Leu;

(SEQ ID NO: 3)
Gly Ser Xaa Phe Leu Ser;

(SEQ ID NO: 4)
Gly Ser Xaa Phe Leu Ser Pro;

(SEQ ID NO: 5)
Gly Ser Xaa Phe Leu Ser Pro Glu;

(SEQ ID NO: 6)
Gly Ser Xaa Phe Leu Ser Pro Glu His;

(SEQ ID NO: 7)
Gly Ser Xaa Phe Leu Ser Pro Glu His Gln;

(SEQ ID NO: 8)
Gly Ser Xaa Phe Leu Ser Pro Glu His Gln Lys/Arg;

(SEQ ID NO: 9)
Gly Ser Xaa Phe Leu Ser Pro Glu His Gln Lys/Arg
Ala/Val;

(SEQ ID NO: 10)
Gly Ser Xaa Phe Leu Ser Pro Glu His Gln Lys/Arg
Ala/Val Gln;

(SEQ ID NO: 11)
Gly Ser Xaa Phe Leu Ser Pro Glu His Gln Lys/Arg
Ala/Val Gln Gln;
```

-continued

```
                                         (SEQ ID NO: 12)
Gly Ser Xaa Phe Leu Ser Pro Glu His Gln Lys/Arg

Ala/Val Gln Gln Arg;

(SEQ ID NO: 13)
Gly Ser Xaa Phe Leu Ser Pro Glu His Gln Lys/Arg

Ala/Val Gln Gln Arg Lys;

(SEQ ID NO: 14)
Gly Ser Xaa Phe Leu Ser Pro Glu His Gln Lys/Arg

Ala/Val Gln Gln Arg Lys Glu;

(SEQ ID NO: 15)
Gly Ser Xaa Phe Leu Ser Pro Glu His Gln Lys/Arg

Ala/Val Gln Gln Arg Lys Glu Ser;

(SEQ ID NO: 16)
Gly Ser Xaa Phe Leu Ser Pro Glu His Gln Lys/Arg

Ala/Val Gln Gln Arg Lys Glu Ser Lys;

(SEQ ID NO: 17)
Gly Ser Xaa Phe Leu Ser Pro Glu His Gln Lys/Arg

Ala/Val Gln Gln Arg Lys Glu Ser Lys Lys;

(SEQ ID NO: 18)
Gly Ser Xaa Phe Leu Ser Pro Glu His Gln Lys/Arg

Ala/Val Gln Gln Arg Lys Glu Ser Lys Lys Pro;

(SEQ ID NO: 19)
Gly Ser Xaa Phe Leu Ser Pro Glu His Gln Lys/Arg

Ala/Val Gln Gln Arg Lys Glu Ser Lys Lys Pro Pro;

(SEQ ID NO: 20)
Gly Ser Xaa Phe Leu Ser Pro Glu His Gln Lys/Arg

Ala/Val Gln Gln Arg Lys Glu Ser Lys Lys Pro Pro

Ala;

(SEQ ID NO: 21)
Gly Ser Xaa Phe Leu Ser Pro Glu His Gln Lys/Arg

Ala/Val Gln Gln Arg Lys Glu Ser Lys Lys Pro Pro

Ala Lys;

(SEQ ID NO: 22)
Gly Ser Xaa Phe Leu Ser Pro Glu His Gln Lys/Arg

Ala/Val Gln Gln Arg Lys Glu Ser Lys Lys Pro Pro

Ala Lys Leu;

(SEQ ID NO: 23)
Gly Ser Xaa Phe Leu Ser Pro Glu His Gln Lys/Arg

Ala/Val Gln Gln Arg Lys Glu Ser Lys Lys Pro Pro

Ala Lys Leu Gln;

(SEQ ID NO: 24)
Gly Ser Xaa Phe Leu Ser Pro Glu His Gln Lys/Arg

Ala/Val Gln Gln Arg Lys Glu Ser Lys Lys Pro Pro

Ala Lys Leu Gln Pro;
or
                                         (SEQ ID NO: 25)
Gly Ser Xaa Phe Leu Ser Pro Glu His Gln Lys/Arg

Ala/Val Gln Gln Arg Lys Glu Ser Lys Lys Pro Pro

Ala Lys Leu Gln Pro Arg,
``` wherein Xaa is A, the modified serine as defined above. Any of the above-listed amino acids may be replaced by a suitable unnatural amino acid, e.g., as described in *Chemistry and Biochemistry of Amino Acids, Peptides and Proteins*, Vol. 7, ed. B. Weinstein (1983), incorporated herein by reference.

The polypeptide sequence may correspond to the sequence of ghrelin specific to the species to be immunized, and having the modified serine at position 3 as described herein. It is known that only 5 out of 28 amino acid residues changes from species to species in mammals, and that the GHSR1 receptor-relevant N-terminal ghrelin(1-10) sequence is completely conserved in mammals and birds. As ghrelin polypeptides are generally conserved between mammalian species (with at least 75% sequence identity) and have only slight variations in sequence identity, cross-reactivity between peptides and species is also contemplated.

Variants of the above-listed amino acid sequences are also contemplated. The variants can be prepared, for example, by synthesizing the desired ghrelin polypeptide variant, or introducing appropriate nucleotide changes into DNA encoding the ghrelin polypeptide constructs of the invention encoding DNA, or isolated from naturally occurring sources.

The sequences of any of the above listed amino acid sequences can be compared and aligned to other known sequences of ghrelin polypeptide that can be provided, for example, by GenBank (accessible on the Internet at www-ncbi-nlm-nih-gov), and locations of amino acid positions for substitutions can be identified as those positions that show a high degree of variability in amino acids, i.e. at least 3 different amino acids are found at that position when different sequences are aligned and compared or have a lower percentage of sequence identity i.e. less than 90% sequence identity. When sequences are aligned, the positions that show variability can either have conservative amino acid substitutions or non-conservative amino acid substitutions. If the position has conservative amino acid substitutions, that would indicate that the amino acid substituted at that position should be of the same type as those observed to be at that position in naturally occurring proteins. For examples of such substitutions, see Table 1. In particular embodiments, conservative substitutions of interest are shown in Table 1 under the heading of preferred substitutions.

TABLE 1

| Original Residue | Exemplary Substitutions | Preferred Substitutions |
| --- | --- | --- |
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro; ala | ala |
| His (H) | asn; gln; lys; arg | arg |
| Ile (I) | leu; val; met; ala; phe; norleucine | |
| Leu (L) | norleucine; ile; val; met; ala; phe | ile |
| Lys (K) | arg; gln; asn | arg |
| Met (M) | leu; phe; ile; norleucine | leu |
| Phe (F) | leu; val; ile; ala; type | leu |
| Pro (P) | ala | ala |
| Ser (S) | thr | thr |
| Thr (T) | ser | ser |

TABLE 1-continued

| Original Residue | Exemplary Substitutions | Preferred Substitutions |
|---|---|---|
| Trp (W) | tyr; phe | tyr |
| Tyr (Y) | trp; phe; thr; ser | phe |
| Val (V) | ile; leu; met; phe; ala; norleucine | leu |

Amino acid substitutions can be the result of replacing one amino acid with another amino acid having similar structural and/or chemical properties, such as the replacement of a leucine with a serine, i.e., conservative amino acid replacements. Insertions or deletions can optionally be in the range of about 1 to 5 amino acids. The variation allowed can be determined by systematically making insertions, deletions or substitutions of amino acids in the sequence and testing the resulting variants for activity exhibited by the source molecule. Preferably, variants have a biological activity of full-length ghrelin polypeptide.

Spacer Moieties

The spacer moieties (C) of the present invention comprise a sequence of 1 to about 5 amino acids comprising one or more polyethylene glycol (PEG) units. PEG is a useful spacer moiety because of its specific properties, i.e. water solubility, high mobility in solution, lack of toxicity and immunogenicity, ready clearance from the body and altered distribution in the body. While PEGylation is known to promote solubility of therapeutic proteins, PEGylation is also known to decrease the immunogenicity of therapeutic proteins (see, e.g., Abuchowski et al., *J. Biol. Chem.* 252 (11): 3582-86 (1977)). It has been found that ghrelin-derived polypeptides comprising a spacer moiety containing one of more PEG units improves the solubility of the ghrelin-derived polypeptide and provides ghrelin-derived polypeptides with surprisingly improved immunogenicity.

The spacer moiety comprises 1 to about 5 consecutive PEG amino acid spacers, the spacer length being from 1 to about 40 PEG units with the total number of PEG units in the spacer moiety not exceeding 40. A PEG amino acid spacer comprises a compound bearing and amino group and a carboxyl group, which are separated by one or multiple units of PEG, that is suitable for incorporation into ghrelin polypeptide sequence. The spacer moiety can include about 1, about 2, about 3, about 4, or about 5 PEG amino acid spacers. For example, the spacer moiety can include 1 PEG-40 amino acid spacer, or 2 PEG-20 amino acid spacers, or 5 PEG-8 amino acid spacers.

The PEG units can be linear, branched, or multiply branched. The PEGylation reagents can contain different lengths of PEG units, such as for example, 4 units, 8 units, 12 units, 24 units, 30 units and the like. The PEG unit can be defined by the following structure:

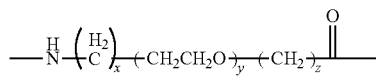

wherein x is between 0 and 1 inclusive, y is between 1 and 40 inclusive, and z is between 1 and 3 inclusive. In an embodiment, the spacer moiety comprises about 1 to about 40 PEG units. In another embodiment, the spacer moiety comprises about 1 to about 4 PEG units, about 1 to about 8 PEG units, about 1 to about 12 PEG units, about 1 to about 24 PEG units, or about 1 to about 30 PEG units. In an embodiment, the PEG unit comprises the following structure:

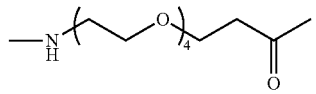

The spacer moiety can be defined by the following structure, wherein p is the number of PEG amino acid spacers:

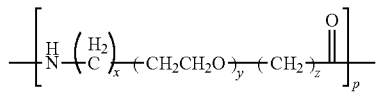

wherein x is between 0 and 1 inclusive, y is between 1 and 40 inclusive, z is between 1 and 3 inclusive, p is between 1 and 5 inclusive, and p*y is 40 or less.

In an embodiment, y is between 1 and about 30 inclusive. In an embodiment, y is between about 1 to about 24 inclusive. In an embodiment, y is between 1 and about 12 inclusive. In yet another embodiment, y is between 1 to about 8 inclusive. In an embodiment, x is between 0 and 1, y is between 1 and 8, z is between 1 and 3 and p is between 1 and 5.

In another embodiment, the spacer moiety comprises the following structure, wherein p is the number of PEG amino acid spacers:

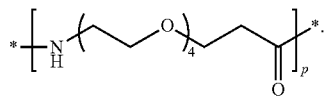

The spacer moieties of the invention can be made by a process known as PEGylation, where ethylene glycol or ethylene oxide polymer units are chemically coupled to the PEG amino acid subsequence. The process of PEGylation is known to those of skill in the art, and is described in detail in, for example, *The Handbook of Pharmaceutical Biotechnology*, S. Cox ed., Wiley (2007). The first step of the PEGylation is the suitable functionalization of the PEG polymer at one or both terminals. PEGs that are activated at each terminus with the same reactive moiety are known as "homobifunctional", where as if the functional groups present are different, then the PEG derivative is referred as "heterobifunctional" or "heterofunctional." The chemically active or activated derivatives of the PEG polymer are prepared to attach the PEG to the desired molecule. The choice of the suitable functional group for the PEG derivative is based on the type of available reactive group on the molecule that will be coupled to the PEG. Reagents used for PEGylation of proteins can include linear or branched PEG, with amine-reactive or sulfhydryl-reactive groups. These include, for example, lysine, cysteine, histidine, arginine, aspartic acid, glutamic acid, serine, threonine, tyrosine. The N-terminal amino group and the C-terminal carboxylic acid can also be used. The PEGylation reagents can contain different lengths of PEG units, such as for example, 4 units, 8 units, 12 units, 24 units, 30 units and the like.

Conjugation and Linker Moieties

The conjugation moiety (D) comprises chemical functionality suitable for conjugation with the linker moiety (E) or directly with the protein carrier moiety (F). As is known in the art, there is a wide range of available methods for conjugating polypeptides to carrier moieties and/or linker moieties, any of which are suitably adapted for use with the invention. Most strategies involve conjugating the polypeptide to a derivatized molecule on the carrier moiety via formation of a covalent bond between reactive groups on the polypeptide and carrier. Suitably, one or more amino acids having a reactive group incorporated in the polypeptide sequence is used to link the polypeptide to the carrier moiety or linker moiety. Suitable conjugation moieties are those having amino groups, carboxyl groups or sulfhydryl groups. As will be appreciated, functional groups of amino acids in the sequence of the polypeptide haptens of the invention may be used as a conjugation moiety to couple the polypeptide haptens to the carrier moiety or linker moiety. Such amino acids may include lysine, arginine, cysteine, aspartate, glutamate, tyrosine and/or histidine. In an embodiment, the conjugation moiety comprises Cys, Lys, Asp, or Glu.

Disulfide coupling using cysteine residues outside the antibody binding domain of the polypeptide haptens of the invention is one particularly suitable coupling strategy, wherein the cysteine is suitably introduced using standard recombinant technology. In one embodiment, a cysteine residue is positioned at a terminus of the polypeptide hapten, e.g., the carboxy or amino terminus. Additional suitable means of conjugating polypeptide moieties to carrier moieties or linker moieties are known in the art and may be used with the present invention.

If the conjugation moiety (D) is not suitable for conjugation directly with the carrier moiety (F), a linker moiety (E) comprising chemical functionality suitable for conjugation with the conjugation moiety and protein moiety can be used. As is known in the art, there is a wide range of available methods for linking conjugation moieties to carrier moieties, any of which are suitably adapted for use with the invention. In an embodiment, the linker moiety comprises a N-maleimidoalkylcarboxyl moiety. In an embodiment, the N-maleimidoalkylcarboxyl moiety comprises N-gamma-maleimidobutyryloxy (GMB) linker. Alternative linker moieties suitable for the ghrelin hapten-to-protein carrier conjugations described herein include carbonyl (such as an aldehyde or a ketone functionalities) and hydroxylamine groups, suitable for oxime-forming conjugation as described by Rose, *J. Am. Chem. Soc.*, 116: 30-33 (1994). Other suitable conjugation methods include "click" ligation, which requires an azide and an alkyne linker moieties (Rodionov, et al. *J. Am. Chem. Soc.*, 129: 12696-12704 (2007)); and a Staudinger ligation, which requires an azide and a carboxyl linker moieties (Saxon, et al. Science 287: 2007-2010 (2000)).

Carrier Moieties

The immunoconjugates of the invention comprise polypeptide haptens covalently or non-covalently conjugated to a carrier moiety (F), using conventional methods. A "carrier moiety," as used herein, refers to a conjugation partner capable of enhancing the immunogenicity of a polypeptide, such as a hapten, for example. For instance, polymers can be used, e.g. carbohydrates such as dextran, mannose or mannan. Integral membrane proteins from, e.g., *E. coli* and other bacteria are also useful conjugation partners. Suitable carriers are typically large, slowly metabolized macromolecules such as proteins; polysaccharides (such as latex functionalized SEPHAROSE™, agarose, cellulose, cellulose beads and the like); polymeric amino acids (such as polyglutamic acid, polylysine, and the like); amino acid copolymers; and inactive virus particles or attenuated bacteria, such as *Salmonella*. Especially useful carrier proteins are serum albumins, keyhole limpet hemocyanin (KLH), certain immunoglobulin molecules, thyroglobulin, ovalbumin, bovine serum albumin (BSA), tetanus toxoid (TT), and diphtheria toxoid (CRM).

In some embodiments, the carrier proteins KLH, TT and CRM are used to form immunoconjugates with the polypeptide haptens respectively. A simple one-step coupling can be performed using the crosslinker EDC to covalently attach carboxyls to primary amines. The carrier proteins can be activated with the crosslinker Sulfo-SMCC, which converts lysine residues to sulfhydryl-reactive maleimide groups. A sulfhydryl-containing hapten can then be reacted with the KLH to complete the immunogen without causing polymerization. The specificity of this reaction is ideal for situations where the cysteine is located away from the desired epitope (e.g. in peptides where a terminal cysteine can be added to either end of the peptide). Maleimide-activated carrier proteins, such as maleimide-activated KLH, for example, where the first part of this two step procedure has been completed, are commercially available.

One or more polypeptide haptens of the invention can be conjugated to the carrier moiety. In an embodiment, about 10 to about 30 copies, about 15 to about 30 copies, about 20 to about 30 copies, about 22 to about 30 copies, about 15 to about 25 copies, about 15 to about 20 copies, about 13 to about 17 copies, or about 16 to about 18 copies of the polypeptide haptens of the invention can be conjugated to a carrier moiety.

Immunogenic Compositions

Immunoconjugates of the ghrelin mimetic polypeptide haptens of the invention are suitably included in an immunogenically effective amount in a composition with a physiologically acceptable vehicle. A "physiologically acceptable" vehicle is any vehicle that is suitable for in vivo administration (e.g., oral, transdermal or parenteral administration) or in vitro use, i.e., cell culture. An "immunogenically effective amount," as used herein, is an amount of an immunoconjugate which is capable of inducing an immune response in an animal and/or an immune response in an animal which significantly engages agents that share immunological features with the immunogen, i.e., native, endogenous ghrelin. The actual amount of the polypeptide hapten may vary depending on the animal to be immunized, the route of administration and adjuvants. Immunogenic dosages can be determined by those of skill in the art. The immune response may be indicated by T and/or B cell responses. Typically, the immune response is detected by the presence of antibodies that specifically bind to a particular ghrelin-derived polypeptide. Methods of detecting antibodies are known to those of skill in the art and include such assays as ELISA assays, ELISPOT assays, western blot assays, and competition assays.

Methods for determining the immunogenicity of a polypeptide are known. For examples, subject animals are boosted with ½ to ¹⁄₁₀ the original amount of the polypeptide hapten of the invention or immunoconjugate thereof in an appropriate adjuvant using subcutaneous injection at multiple sites. The animals are bled after a specific period of time, and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions.

Compositions comprising the immunoconjugates of the invention may be formulated for in vivo use, i.e., therapeutic or prophylactic administration to a subject. These compositions can be administered by a variety of routes including oral, rectal, transdermal, subcutaneous, intravenous, intramuscular, and intranasal. The compositions are effective as both injectable and oral compositions. Immunogenic compositions of the invention, such as vaccines, are conventionally administered parenterally, by injection, for example, subcutaneously, intracutaneously, intradermal, subdermally or intramuscularly. Formulations are prepared in a manner well known in the pharmaceutical art and comprise the ghrelin hapten immunoconjugates of the invention as the active ingredient. In particular embodiments, the compositions are formulated as vaccine compositions. As used herein, a "vaccine" is a composition that is capable of inducing an immune response in a subject, including but not limited to, the production of sequestering antibodies.

Preparation of immunogenic compositions, such as vaccines, that contain polypeptide sequences as active ingredients is generally well understood in the art, as exemplified by U.S. Pat. No. 4,608,251, incorporated herein by reference. Typically, such immunogenic compositions are prepared as injectables, either as liquid solutions or suspensions. Solid forms suitable for formulation in solution or suspension prior to injection may also be prepared. The preparation may also be emulsified. The immunoconjugates of the invention may be mixed with excipients which are pharmaceutically acceptable and compatible with the active ingredient. Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, methyl cellulose, and combinations thereof. The immunogenic compositions of the invention can additionally include: pH buffering agents; lubricating agents such as talc, magnesium stearate, and mineral oil; wetting agents; emulsifying and suspending agents; and preserving agents such as methyl- and propylhydroxy-benzoates.

In some embodiments, immunogenicity is enhanced by formulating the immunogenic compositions of the invention with an adjuvant. Adjuvants and their use are well known in the art. Various methods of achieving an adjuvant effect are known. General principles and methods are detailed, for example, in *The Theory and Practical Application of Adjuvants*, 1995, Duncan E. S. Stewart-Tull (ed.), John Wiley & Sons Ltd, ISBN 0-471-95170-6, and also in *Vaccines: New Generation Immunological Adjuvants*, 1995, Gregoriadis G et al. (eds.), Plenum Press, New York, ISBN 0-306-45283-9, both of which are hereby incorporated by reference herein. A particularly suitable adjuvant for use with the invention is aluminum hydroxide or phosphate (alum), commonly used as 0.05 to 0.1 percent solution in buffered saline.

Methods of Use

The polypeptide haptens and immunogenic compositions of the invention are useful for inducing an anti-ghrelin immune response in a subject. Inducing an anti-ghrelin immune response in a subject in accordance with the invention may be accomplished by administering to the subject the immunoconjugate compositions described above. An anti-ghrelin immune response is suitably assessed by the assays described in the examples below.

A "subject" as used herein is a vertebrate, suitably a mammal, more suitably a human. Suitable subjects may also include domestic animals, e.g., cats, dogs and horses. As will be appreciated, for purposes of study, the subject is suitably an animal model, e.g., a mouse or rat. It will be appreciated that for other species, e.g., dog, cat, horse or mouse, the ghrelin mimetic polypeptide portion of the immunoconjugate can be selected based on species. As used herein, an "anti-ghrelin immune response" specifically refers to inducing a therapeutic or prophylactic ghrelin-sequestering effect that is mediated by the immune system of the subject. Such an immune response suitably promotes clearance or immune control of endogenous ghrelin in the subject such that system-wide effects are observed in the subject, such as prevention or slowing of weight gain, sparing of lean body mass, decreased feed efficiency, and/or decreased relative adiposity.

The polypeptide haptens and immunogenic compositions of the invention are useful for controlling adiposity in a subject. "Controlling adiposity," as used herein, includes, but is not limited to, preventing or slowing of weight gain, sparing lean body mass, decreasing feed efficiency and decreasing relative adiposity in the subject. Methods of controlling adiposity may be accomplished by administering to the subject the polypeptide haptens or immunoconjugate compositions of the invention. In an embodiment, administration of a polypeptide hapten or immunogenic composition of the invention to a subject prevents or inhibits the development of obesity in the subject. In an embodiment, administration of a polypeptide hapten or immunogenic composition of the invention to a subject inhibits weight gain by the subject. In an embodiment, administration of a polypeptide hapten or immunogenic composition of the invention to a subject decreases relative adiposity in the subject. In an embodiment, administration of a polypeptide hapten or immunogenic composition of the invention to a subject inhibits restriction-induced feeding by the subject during low-calorie diet-induced weight loss.

Administration to a subject of the polypeptide haptens or immunoconjugate compositions in accordance with the invention appears to exhibit beneficial effects in a dose-dependent manner. Thus, within broad limits, administration of larger quantities of the immunoconjugate compositions is expected to control adiposity to a greater degree than does administration of a smaller amount. Moreover, efficacy is also contemplated at dosages below the level at which toxicity is seen. Further, in practice, higher doses are generally used where the therapeutic treatment of obesity is the desired end, while the lower doses are generally used for prophylactic purposes or slowing weight gain.

Immunogenic compositions such as vaccines are administered in a manner compatible with the dosage formulation, and in such amount as will be prophylactically or therapeutically effective and immunogenic. It will be appreciated that the specific dosage administered in any given case will be adjusted in accordance with the condition of the subject and other relevant medical factors that may modify the activity of the ghrelin immunoconjugate or the response of the subject, as is well known by those skilled in the art. The quantity to be administered depends on the subject to be treated, including age, body weight, general state of health, direct, timing and mode of administration, the rate of excretion, medicaments used in combination, the capacity of the individual's immune system to mount an immune response, and the degree of protection desired.

Dosages for a given patient can be determined using conventional considerations such as by means of an appropriate conventional pharmacological or prophylactic protocol. The maximal dosage for a subject is the highest dosage that does not cause undesirable or intolerable side effects. The number of variables in regard to an individual prophylactic or treatment regimen is large, and a considerable range of doses is expected.

It is anticipated that dosages of immunoconjugate in the range from about 0.1 μg/kg body weight to about 10 mg/kg body weight are contemplated, such as in the range from about 500 μg/kg body weight to about 1000 μg/kg body weight, will prevent or reduce symptoms at least 50% compared to pre-treatment symptoms. It is specifically contemplated that vaccine preparations and compositions of the invention may palliate or alleviate weight gain without providing a cure, or, in some embodiments, may be used to inhibit or prevent obesity. Suitable regimens for initial administration and booster shots are also contemplated and are typified by an initial administration followed by subsequent inoculations or other administrations. In one embodiment, a subject is immunized with the antigen, immunogenic conjugates, or derivatives by combining, e.g., about 0.1 µg/kg body weight of the polypeptide hapten or immunoconjugate with a given volume of adjuvant and injecting the solution intradermally at multiple sites.

It is specifically contemplated that any embodiment of any method or composition of the invention may be used with any other method or composition of the invention.

As used in this specification and the appended claims, the singular forms "a," "an," and "the" include plural referents unless the content clearly dictates otherwise. Thus, for example, reference to a composition containing "a polypeptide" includes a mixture of two or more polypeptides. It should also be noted that the term "or" is generally employed in its sense including "and/or" unless the content clearly dictates otherwise.

It also is specifically understood that any numerical value recited herein includes all values from the lower value to the upper value, i.e., all possible combinations of numerical values between the lowest value and the highest value enumerated are to be considered to be expressly stated in this application. For example, if a range is stated as 1% to 50%, it is intended that values such as 2% to 40%, 10% to 30%, or 1% to 3%, etc., are expressly enumerated in this specification.

EXAMPLES

The following examples are provided to assist in a further understanding of the compositions and methods described herein. The particular materials and conditions employed are intended to be illustrative and not limiting on the reasonable scope of the appended claims.

Example 1. Ghrelin Hapten Immunoconjugate Synthesis

Ghrelin haptens Ghr1, Ghr2, Ghr3, Ghr4 and Ghr5 were synthesized and coupled to the carrier proteins keyhole limpet hemocyanin (KLH), detoxified tetanus toxoid (TT), detoxified diphtheria toxoid (CRM), or bovine serum albumin (BSA). The structures of the Ghrelin haptens and their immunoconjugates are shown in FIG. 1. A schematic representation of the haptens Ghr1-Ghr5, and an exemplary synthesis scheme for haptens Ghr4 (hapten 3) and Ghr5 (hapten 4) are as follows:

Haptens

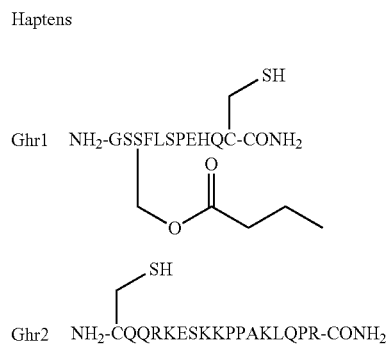

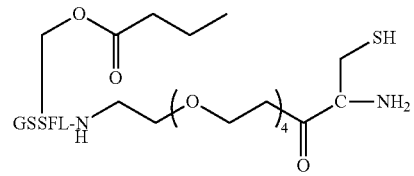

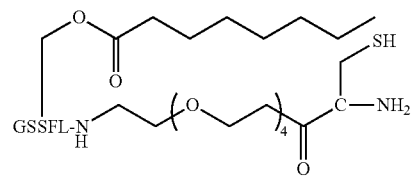

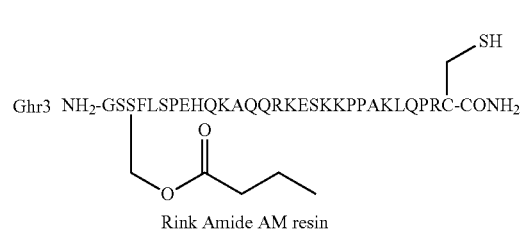

Ghr3 NH$_2$-GSSFLSPEHQKAQQRKESKKPPAKLQPRC-CONH$_2$

Rink Amide AM resin

↓ Fmoc SPPS

Boc-Gly-Ser(tBu)-Ser(TBDMS)-Phe-Leu-dPEG$_4$-Cys(Trt)-NH—◯

1. 0.1M TBAF/DMF
2. octanoic acid/PyBrOP/DIEA/NMP or butyric anhydride/NMP

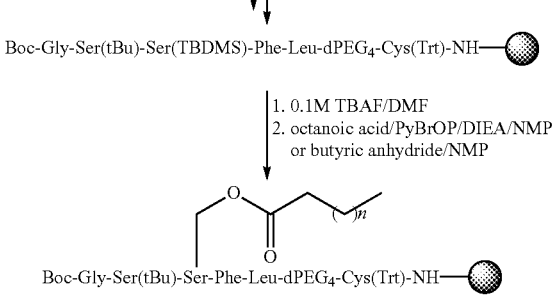

Boc-Gly-Ser(tBu)-Ser-Phe-Leu-dPEG$_4$-Cys(Trt)-NH—◯

TFA/water/TIPS
95:2.5:2.5

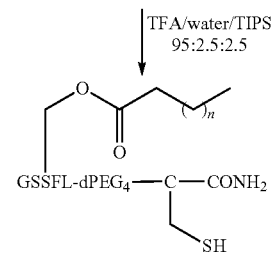

$n = 1, 5$
Haptens 3 & 4

The ghrelin haptens were synthesized using the automated peptide synthesizer (CS Bio, Menlo Park Calif.) by conventional Fmoc solid phase peptide synthesis (SPPS) methodologies, as described in WO 2008/016976, incorporated herein by reference. In a typical procedure, polystyrene-based aminomethyl (PL/AMS) resin (2.0 g, 1.11 mmol/g) was placed into a 50 mL reaction vessel and allowed to swell in DCM (20 mL) for 1 h. Fmoc-Rink amide linker was coupled using the standard HOBt ester activation (3 eq. of Fmoc Rink linker, 3 eq. of 6-Cl-HOBt, and 3 eq. of DIC) in DMF: the ingredients were dissolved in DMF, and agitated by bubbling nitrogen through the solution for 20 min, after which the coupling mixture was transferred into the reaction vessel with the resin and the mixture was agitated for 90 min. The resin was washed with DMF (4×20 mL), and with DCM (3×20 mL). The unreacted amino groups were capped using acetic anhydride (2 mL) and pyridine (2 mL) in DCM (20 mL) for 30 min, and the resin was once again washed with DMF (4×20 mL), and with DCM (3×20 mL). The Fmoc protecting group on the Rink linker was removed with 25% piperidine in DMF (1×5 min and 1×15 min), and the resin was washed with DMF (4×20 mL) and DCM (3×20 mL), after which the first amino acid was coupled using DIC/6-Cl-HOBt activation (3 eq. of Fmoc-AA, 3 eq. of 6-Cl-HOBt, and 3 eq. of DIC) in DMF. The peptide PEGylation was performed using a commercially available N-Fmoc-protected PEG4 amino acid using the procedure outlined above. The same procedure can be used to introduce multiple PEG amino acid spacers. The peptide sequences were completed by consecutively coupling the appropriate amino acids using the procedure described above.

Water-soluble truncated ghrelin haptens were prepared by modification of the pentapeptide haptens Ghr4 and Ghr5. The orthogonal silyl ether protection for the side chain of Ser$^3$ was removed with 0.1 M TBAF in DMF (2×15 min) prior to the Ser$^3$ side chain acylation. The deprotected resin-bound peptide was washed with DMF (2×20 mL), and N-methylpyrrolidinone (NMP, 1×20 mL). The peptide esterifications were accomplished by treatment with butyric anhydride (6 eq.) in NMP (30 mL) or with octanoic acid (6 eq.)/PyBrOP (6 eq.)/DIPEA (12 eq.) in NMP (30 mL). The reaction is accelerated by addition of a catalytic (3-5 mol %) amount of DMAP. Acylations were run for 4 h at room temperature, after which the resin was washed with DMF (4×20 mL) and DCM (3×20 mL). Small samples of peptide-resins were washed thrice with methanol, twice with diethyl ether, dried under vacuum (2 h), and the peptides were cleaved off the solid support with TFA/triisopropylsilane (TIPS)/water (95:2.5:2.5% v/v, 3 h). The resin beads were filtered off, and the filtrates were evaporated under reduced pressure. The solid crude peptide residues were dissolved in methanol and analyzed on API 150EX ESI-Q mass-spectrometer (PE Sciex). The progress of the peptide esterification was estimated by relative intensity of MS peaks corresponding to the acylated and the des-acyl-peptides. The esterifications were repeated until disappearance of the desacyl-peptide signal indicated complete conversion, typically requiring 1-2 acylation cycles.

Upon completion of peptide esterification, the resin was washed with DMF (5×15 mL), DCM (3×15 mL), methanol (5×15 mL), and diethyl ether (5×15 mL), and dried under reduced pressure (16 h). The peptides were cleaved off the solid support with 95% v/v TFA, 2.5% water, 2.5% TIPS (30 mL, 3 h), and the crude peptides were precipitated out by the dropwise addition of the peptide-TFA solution to a chilled 3:1 mixture of diethyl ether and petroleum ether (4×30 mL), which gave white precipitates. The resulting peptide suspensions were centrifuged for 10 min at 6,500 rpm, and the liquid was decanted. The crude peptides were washed with diethyl ether/centrifuged/decanted four more times, and after the final centrifugation, the peptides were dried under vacuum (2 h).

Peptide purification was accomplished by preparative RP-HPLC on a $C_{18}$-bonded silica column (Vydac 218TP152022, 250×22 mm, 15-20 μm, 300 Å) using a Shimadzu SCL-10A HPLC system. The peptides were eluted with the following linear gradients of acetonitrile (with 0.09% TFA) in 0.1% aqueous TFA at 10 mL/min flow rate. The purified peptides were isolated in 40-50% overall yield. The purity of the peptides was checked by analytical reverse-phase HPLC using a Vydac $C_{18}$ 218TP104 column (Western Analytical Products, Murrieta, Calif.) monitored at 214 nm using a linear gradient of 10-90% acetonitrile (with 0.09% TFA) in 0.1% aqueous TFA over 40 min with 1.0 mL/min flow rate at 35° C., while a of 2-20% acetonitrile linear gradient was used for hapten 2 (Ghr2).

The protein carrier conjugates were prepared via a maleimide-thiol solution-phase coupling, as shown in the following reaction scheme:

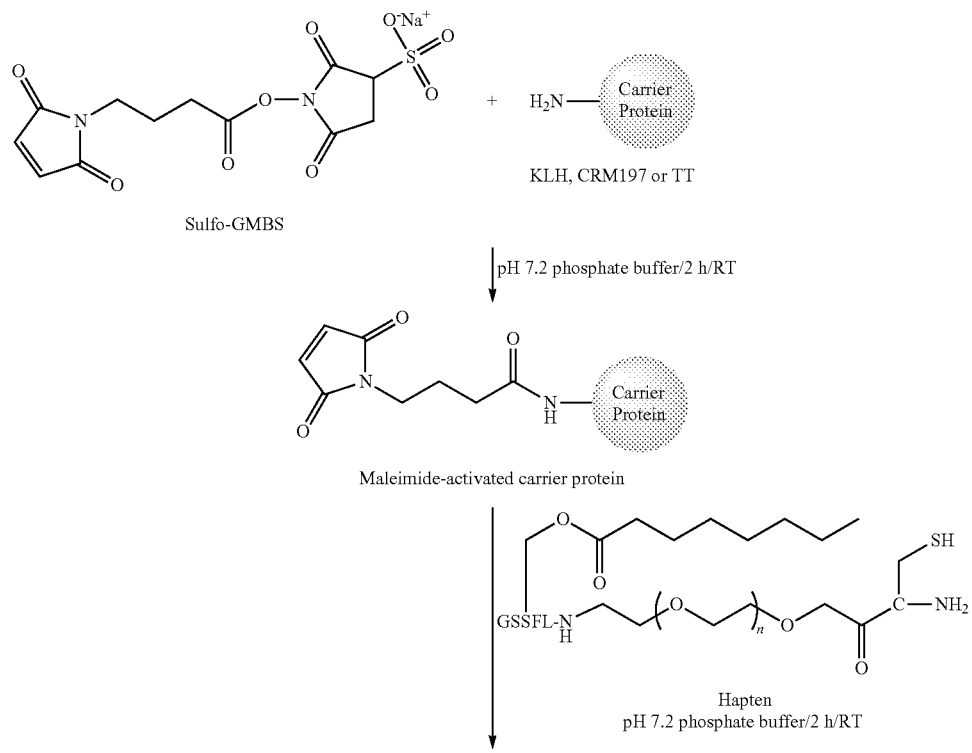

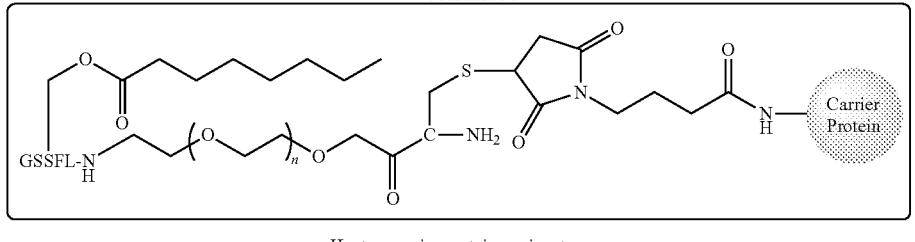

Hapten-carrier protein conjugate
Purified by dialysis with a pH 6.5 PBS buffer

The protein carriers were preactivated by an established methodology shown in the above reaction scheme, in which the protein carriers were dissolved in or diluted with Pierce Conjugation Buffer (pH 7.2 PBS buffer; the chemistry will work in other amine-free buffers with the pH range of 7-9, typically pH 6.5-7.5 is used) to give about 5 mg/mL protein concentration. Water-soluble maleimide-bearing sulfo-GMBS linker (Pierce), taken in about 10-fold excess to the protein, was dissolved in Pierce Conjugation Buffer to obtain about 10 mg/mL concentration. For example, 20 mg/mL KLH protein solution (200 μL, 4 mg) was diluted with 500 μL conjugation buffer, and sulfo-GMBS (2.5 mg) was dissolved in 300 μL conjugation buffer, and added to the KLH solution to achieve ~4 mg/mL KLH concentration. The protein and the sulfo-GMBS solutions were mixed and agitated by gentle shaking for 2 h at room temperature, or for 12 h at 4° C. The excess linker was removed by dialysis using Pierce 10K MWCO Slide-A-Lyzer dialysis cassettes and pH 7.4 PBS buffer. To ensure effective purification, the buffer was changed 2-3 times at 4-5 h intervals.

Sulfhydryl-containing hapten of the same mass amount as the protein carrier was dissolved in conjugation buffer (depending on the hapten and hapten-protein conjugate solubility, the hapten concentration can be between 2-20 mg/mL). The preactivated protein solution was added and the mixture was agitated by gentle shaking for 2-4 h at room temperature, or for 12-16 h at 4° C. The conjugation time depended on the hapten solubility (less soluble hapten will have lower concentration and will require additional reaction time). For example, ghrelin hapten 1 (4 mg) was dissolved in conjugation buffer (200 μL) and mixed with the maleimide-activated KLH protein solution. Purification of the resulting conjugate was accomplished by dialysis using Pierce 10K MWCO Slide-A-Lyzer dialysis cassettes and pH 7.4 PBS buffer. To ensure effective purification, the buffer was changed 2-3 times at 4-5 h intervals. The total protein in the purified conjugate solutions was determined by microplate Bicinchoninic Acid (BCA) protein assay (Pierce), which is more compatible with sulfur-rich proteins than Lowry assay. This assay is accurate in the range of 20-2,000 μg/ml protein concentration, and the results are generally more accurate if the analyte concentration is around the middle of the calibration curve, so the conjugate samples were tested at three dilutions (1x, 2x, and 3x), in case the conjugate concentration was significantly higher than 2 mg/mL assay limit. The microplate BCA assay used 10 μL of the protein sample and 200 μL of the BCA working reagent (WR), mixed on a 96-well plate, which was then shaken for 30 seconds, and incubated at 37° C. for 30 min. The plate was then cooled and the absorbance was measured at 562 nm on a SpectraMAX 250 plate reader (Molecular Devices). The assay was calibrated using the BSA standard provided in the Pierce BCA assay kit in the range of 20-2,000 μg/ml protein concentration, and the protein conjugate concentrations were determined by comparing the measured absorbances with the standard calibration curve.

The efficacy of hapten conjugations to CRM197 (63 kDa), TT (150 kDa) and BSA (67 kDa) proteins was monitored by MALDI-TOF MS analyses, while KLH protein ($4.5 \times 10^5$-$1.3 \times 10^7$ Da) was too large for MS analysis. The extent of conjugation was estimated as follows: (mass of the conjugate−mass of the protein carrier)/(calculated mass of the hapten+linker). Typical range for hapten conjugation was between 13-17 hapten copies for CRM197, 22-30 copies for TT, and 16-18 copies for BSA.

Example 2. Solubility and Hydrolytic Stability of Ghrelin Haptens and Conjugates To test the water solubility of the haptens and their immunoconjugates, the Ghrelin hapten constructs (with or without the spacer moiety) and immunoconjugates of these haptens were dissolved in water at a concentration of 1 mg/mL, and the solubility at different pH values and a temperature of 25° C.

Table 2 shows the solubility of Ghr1, Ghr2, Ghr4, Ghr5, and PEGylated versions of Ghr4 and Ghr5 at pH values of pH 5, pH6 and pH7.

TABLE 2

Solubility of Ghrelin Haptens as a function of pH

| Haptens | pH5 | pH6 | pH7 |
|---|---|---|---|
| Ghr1 (GSS(butyryl)FLSPEHQC-NH2) | X | X | X |
| Ghr2 (CQQRKESKKPPAKLQPR-NH2) | X | X | X |
| Ghr4 (GSS(butyryl)FLC-NH2) | | X | <0.1 mg/mL |
| Ghr5 (GSS(octanoyl)FLC-NH2) | | | |

TABLE 2-continued

Solubility of Ghrelin Haptens as a function of pH

| Haptens | pH5 | pH6 | pH7 |
|---|---|---|---|
| PEG-Ghr4 (GSS(butyryl)FL-PEG$_4$-C-NH2) | X | X | X |
| PEG-Ghr5 (GSS(octanoyl)FL-PEG$_4$-C-NH2) | X | X | ~0.4 mg/mL |

As shown in Table 2, Ghr4 and Ghr5 pentapeptide haptens are only minimally soluble, with Ghr4 hapten being insoluble at pH5, soluble at pH 6 and only minimally soluble at pH7. Ghr5 hapten is insoluble at all pH5, pH6, and pH7. In contrast, Ghr4 comprising the spacer moiety is fully soluble (to a concentration of 1 mg/mL) at pH5, pH6 and pH7, and the Ghr5 comprising the spacer moiety is fully soluble at pH5 and pH6 and partially soluble at pH7.

Table 3 shows the solubility of ghrelin immunoconjugates with carrier proteins KLH and BSA at pH 7.4 at 25° C.

TABLE 3

Solubility of Ghrelin Immunoconjugates

| Haptens | KLH | BSA |
|---|---|---|
| Ghr1 (GSS(butyryl)FLSPEHQC-NH2) | X | X |
| Ghr2 (CQQRKESKKPPAKLQPR-NH2) | X | X |
| Ghr4 (GSS(butyryl)FLC-NH2) | | |
| Ghr5 (GSS(octanoyl)FLC-NH2) | | |
| PEG-Ghr4 (GSS(butyryl)FL-PEG$_4$-C-NH2) | X | X |
| PEG-Ghr5 (GSS(octanoyl)FL-PEG$_4$-C-NH2) | partial | partial |

Table 3 indicates that Ghr4-KLH and Ghr5-KLH immunoconjugates are insoluble in water. Similarly, the Ghr4-BSA and Ghr5-BSA immunoconjugates are also insoluble in water. In contrast, PEGylated Ghr4-KLH and PEGylated Ghr4-BSA immunoconjugates are fully soluble in water (to a concentration of 1 mg/mL), and PEGylated Ghr5-KLH and PEGylated Ghr5-BSA immunoconjugates are partially soluble in water.

The data in Table 2 and Table 3 support the observation that incorporation of the spacer moiety into the ghrelin haptens increases the solubility of these constructs in water. Furthermore, immunoconjugates of ghrelin hapten comprising the spacer moiety also show increased solubility in water.

Figure 2:
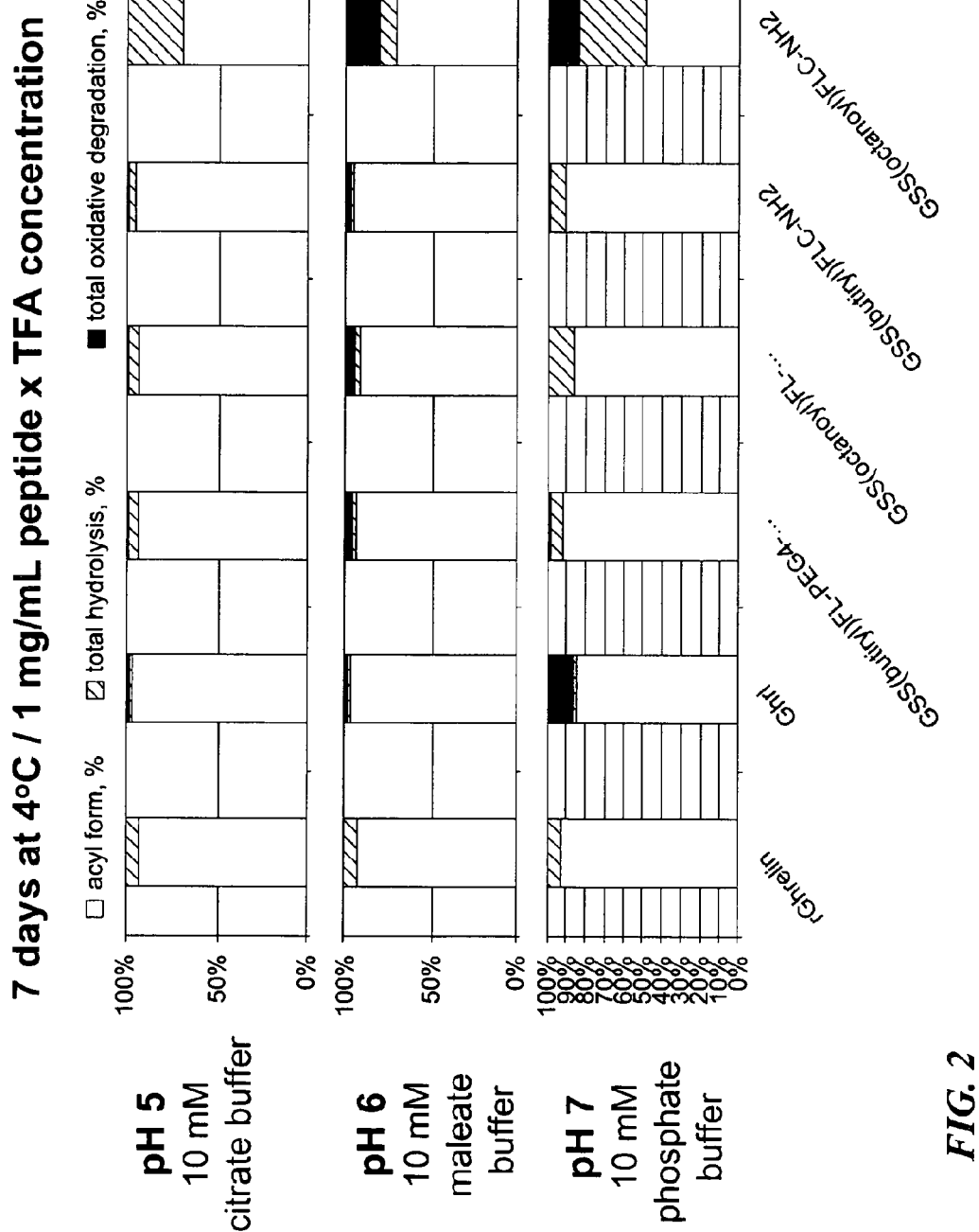
FIG. 2 is a graphical representation of the percentage of active acyl form of each ghrelin hapten present after seven days compared to the percentage of total hydrolysis and oxidative degradation observed for each hapten.

To test the hydrolytic stability of the Ghrelin haptens, 1 mg/mL solutions of Ghr1, Ghr4, Ghr5 and the corresponding Ghr4 and Ghr5 haptens comprising the spacer moiety (PEG-Ghr4 and PEG-Ghr5 respectively) were maintained in buffered solutions for 7 days at either 4° C. or 37° C. at pH values of pH5 (in 10 mM citrate buffer), pH6 (in 10 mM maleate buffer) or pH7 (in 10 mM phosphate buffer). FIG. 2 is a graphical representation comparing the percentage of the active acyl form of each Ghrelin hapten present after seven days with the percentage of total hydrolysis and the percentage of total oxidative degradation for each hapten.

As can be seen from FIG. 2, the PEG-Ghr5 shows less hydrolysis and significantly reduced oxidative degradation relative to Ghr5 without the spacer moiety. For example, PEG-Ghr5 maintained at pH 5 for 7 days at 4° C. showed approximately the same amount of hydrolysis as the native protein (rGhrelin), and significantly less oxidative degradation than the corresponding Ghr5 hapten. This data, taken together with the data shown in Tables 2 and 3, demonstrates that incorporation of the spacer moiety improves solubility and hydrolytic stability of the Ghr5 hapten construct.

Example 3. Specificity and Binding Affinity of Ghrelin Haptens and Conjugates

Subjects and Protocol for Vaccination

Mice (C57BL/6J, obtained from Jackson Laboratories, Bar Harbor, Me.) were individually housed in a 12 h:12 h lit (0600 lights on), humidity-(60%) and temperature-controlled (22° C.) vivarium with continuous access to chow and water. The pelleted chow diet (LM-485 Diet 7012; Harlan Teklad, Madison Wis., USA) is a corn-based extruded cereal comprised of 65% carbohydrate, 13% fat, 21% protein, metabolizable energy 3.41 kcal/g. Procedures adhered to the National Institutes of Health Guide for the Care and Use of Laboratory Animals (NIH Pub. No. 85-23, revised 1996) and the "Principles of laboratory animal care" (http://www.nap.edu/readingroom/bookslabrats) and were approved by the Institutional Animal Care and Use Committee of The Scripps Research Institute.

Age- and weight-matched mice were immunized using protocols of our laboratory as described in Qi et al., $\Delta^9$-Tetrahydrocannabinol immunochemical studies: Haptens, monoclonal antibodies, and a convenient synthesis of radiolabeled $\Delta^9$-Tetrahydrocannabinol, J. Med. Chem. 48: 7389-99 (2005). Immunization involved five (5) immunizations over ten (10) weeks. Age and weight-matched mice received immunizations (i.p. 0.2 mL) 90 min before the dark cycle on experimental days 0, 14 (2 weeks), 28 (4 weeks), 49 (7 weeks) and 70 (10 weeks). All immunizations used ALUM (Pierce) as the adjuvant, and contained 50 μg of protein (i.e. immunoconjugates of Ghr1, Ghr2, PEG-Ghr4 and PEG-Ghr5 peptides with carrier proteins KLH, TT or CRM197). Tail blood was collected one week post-immunization, centrifuged and plasma analyzed for antibody titers and ghrelin binding affinity.

For the purpose of this example, the various ghrelin haptens are identified as follows:

```
Hapten 1.
Ghr1:       GSS(butyryl)FLSPEHQC-NH2

Hapten 2.
Ghr2:       CQQRKESKKPPAKLQPR-NH2

Hapten 3.
PEG-Ghr4:   GSS(butyryl)FL-PEG4-C-NH2

Hapten 4.
PEG-Ghr5:   GSS(octanoyDFL-PEG4-C-NH2
```

The ghrelin immunoconjugates (i.e. the above four haptens, each combined with the three carrier proteins KLH, TT, or CRM197) are labeled accordingly as KLH1, KLH2, KLH3, KLH4, TT1, TT2, TT3, TT4, and CRM1, CRM2, CRM3, CRM4).

Plasma antibody titers were determined using ELISA. ELISA plates (96-well, COSTAR 3590) containing 3 ng per well Ghr3-BSA in 50 μL of 10 mM PBS, pH 7.2, were dried overnight, followed by routine ethanol fixing and blocking with blotto in PBS. Mice plasma samples were serially diluted beginning with a 1:100 dilution in blotto. Plasma binding was allowed to take place for 1 hour in a moist chamber at 37° C. After washing, 200 ng per well goat anti-rat Gig conjugated with alkaline phosphates (Southern Biotech) in 50 μL PBS-blotto was added and incubated for 1 hour in a moist chamber at 37° C. The plates were thoroughly washed with water, air dried and developed by adding 200 μL per well of 200 am p-nitrophenylphosphate (Pierce) in 100 mM MOPS, pH 7.4. After 3 hours at room temperature, the absorbance was measured at 405 nm in a microplate reader (Molecular Devices).

Ghrelin specificity of plasma was determined using two assays: an equilibrium dialysis assay and a competition ELISA. Equilibrium dialysis was performed using serial dilutions of [$^{125}$I]-rat ghrelin (Ser-3-n-octanoyl, Bachem, diluted in situ with non-labeled ghrelin) as ligand and constant plasma amounts (1:1 dilution in PBS, pH 7.4). Wells in one microtiter plate (12 per sample) were filled with 170 μL of radiolabeled ghrelin in PBS, and a second plate was prepared with wells containing plasma of mice (that were immunized with the ghrelin-carrier immunoconjugates or just the carrier) in PBS (170 μL/well). The two plates were tightly connected with filled wells facing each other and separated with a dialysis membrane (cutoff 14 kDa). The plates were attached vertically to a shaker and were shaken for 24 h at room temperature, after which they were carefully separated. The membrane was discarded and from each well 100 μL was transferred to tubes for γ-radiation counting. The average in differences in DPM (disintegrations per minute) between opposite wells was determined for each dilution of ghrelin, yielding apparent binding constants ($K_{d-app}$).

Figure 3:
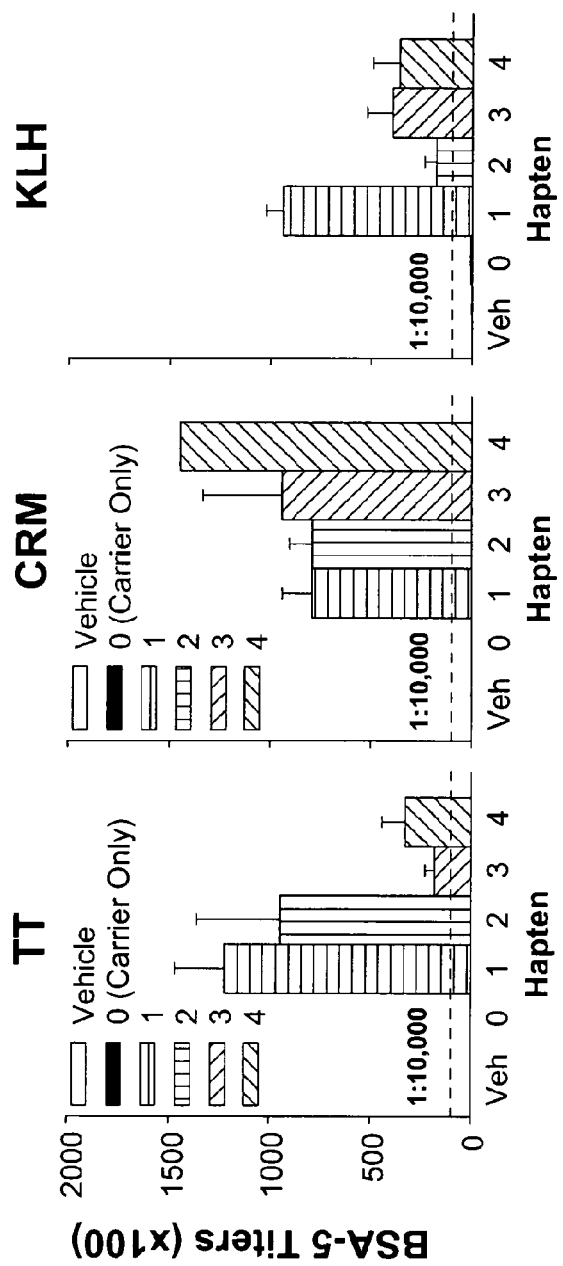
FIG. 3 is a graphical representation of ghrelin hapten titers against BSA-acylated ghrelin in plasma collected from animals from the 5$^{th}$ bleed after immunization with the ghrelin haptens.
Figure 4:
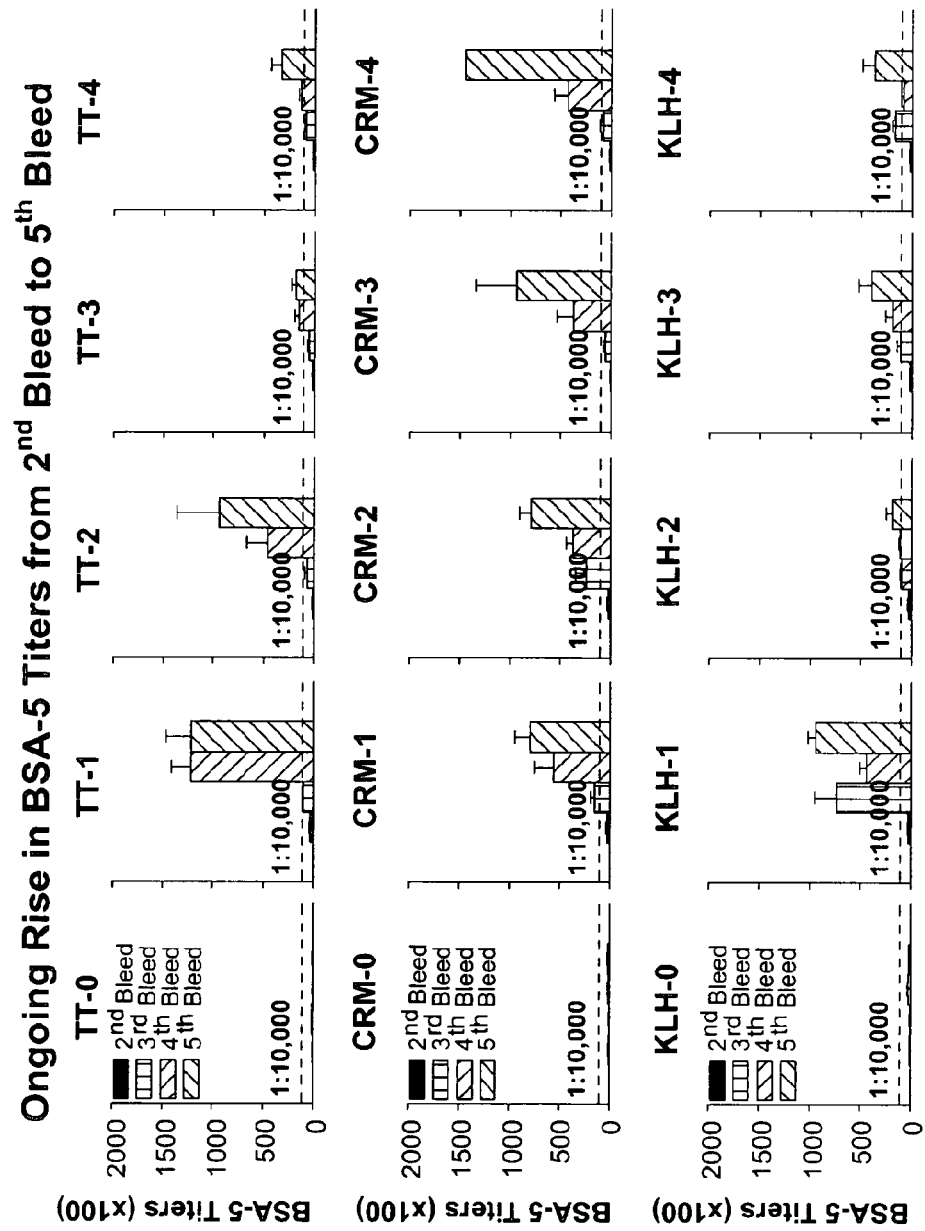
In FIG. 4, 0=carrier only; 1=GSS(butyryl) FLSPEHQC-NH$_2$ (SEQ ID NO:26); 2=CQQRKESKKP-PAKLQPR-NH$_2$ (SEQ ID NO:27); 3=GSS(butyryl)FL-PEG$_4$-C—NH$_2$ (SEQ ID NO:31; and 4=GSS(octanoyl)FL-PEG$_4$-C—NH$_2$ (SEQ ID NO:32).

Results are shown in FIG. 3 and FIG. 4. FIG. 3 is a graphical representation of Ghr hapten titers against BSA-acylated ghrelin in plasma from the $5^{th}$ bleed following immunization. FIG. 4 is a graphical representation comparing the plasma titers after the $2^{nd}$, $3^{rd}$, $4^{th}$ and $5^{th}$ bleeds for the various ghrelin immunoconjugates. The data in these figures demonstrate that the ghrelin immunoconjugates produced significant immune response by the fifth bleed, with the titers against BSA-5 at or exceeding the 1:10,000 titer threshold associated with functional activity, as reported in Zorrilla et al., Proc. Natl. Acad. Sci. 103: 13226-31 (2006). PEGylation is known to decrease the antigenicity of therapeutic proteins. Surprisingly, the PEG-Ghr immunoconjugates induced titers comparable to the non-PEGylated Ghr1 and Ghr2 immunoconjugates. Similarly, in FIG. 4, it can be seen that BSA-5 titers for all Ghr5 immunoconjugates (hapten 4) rises progressively from the $2^{nd}$ immunization (bleed) to the $5^{th}$ immunization.

For competitive ELISA, plates (96-well) were coated overnight at 4° C. with freshly prepared ghrelin-BSA conjugate. The plates were blocked with 4% skim milk, washed and plasma samples were added at appropriate dilutions. The plates were washed and Ser-3-n-octanoyl ghrelin was added to the wells in a concentration series starting at 100 μM. Plates were incubated for 1 h at 37° C., thoroughly washed, and goat anti-mouse-horseradish peroxidase (HRP) conjugate (Pierce) was added. After an incubation period of 1 h at RT, plates were thoroughly washed again and the HRP substrate (TMB substrate kit; Pierce) was added, the reaction was allowed to develop for 15 min and stopped by the addition of 2M H2SO4. The absorbance (450 nm) was read and the values plotted using GraFit (Erithacus Software Ltd). The free antigen concentration at which the absorbance value is 50% of the maximum absorbance was considered the average $K_{d-app}$ of the plasma for ghrelin. Results are shown in Table 4A and Table 4B below.

TABLE 4A

Competition ELISA Results at $3^{rd}$ Bleed

| Carrier Protein | Measure | Hapten 1 | Hapten 2 | Hapten 3 | Hapten 4 |
|---|---|---|---|---|---|
| TT | Ghrelin affinity (μM) | 41.5 + 15.2 | 45.2 + 14.9 | 34.9 + 20.8 | 0.6 + 0.3 |
|  | Selectivity vs. des-ghrelin (fold) | 1.7 | 0.9 | 2.8 | 11.3 |
| CRM | Ghrelin affinity (μM) | 139.6 + 27.3 | 45.2 + 19.1 | 11.3 + 3.5 | 20.7 + 18.0 |
|  | Selectivity vs. des-ghrelin (fold) | 1.1 | 0.9 | 1.3 | 8.0 |
| KLH | Ghrelin affinity (μM) | 83.0 + 12.7 | 4.0 + 1.9 | 49.3 + 32.6 | 0.8 + 0.5 |
|  | Selectivity vs. des-ghrelin (fold) | 6.3 | 1.3 | 1.5 | 22.6 |

TABLE 4B

Competition ELISA Results at 5$^{th}$ Bleed

| Carrier Protein | Measure | Hapten | | | |
|---|---|---|---|---|---|
| | | 1 | 2 | 3 | 4 |
| TT | Ghrelin affinity (μM) | 17.4 + 12.3 | 5.7 + 0.0 | 22.6 + 15.9 | 0.25 + 0.0 |
| | Selectivity vs. des-ghrelin (fold) | 2.2 | 1.0 | 2.8 | 22.6 |
| CRM | Ghrelin affinity (μM) | 152.2 + 43.0 | 2.6 + 0.7 | 13.4 + 5.9 | <0.25 + 0.0 |
| | Selectivity vs. des-ghrelin (fold) | 1.3 | 1.0 | 1.4 | 53.8 |
| KLH | Ghrelin affinity (μM) | 9.0 + 3.3 | 1.4 + 0.0 | 20.7 + 13.8 | 0.25 + 0.1 |
| | Selectivity vs. des-ghrelin (fold) | 3.6 | 1.0 | 1.8 | 17.5 |

For therapeutic purposes, an immunoconjugate that induces high affinity anti-ghrelin antibodies that specifically bind acylated ghrelin is preferred as the inactive, des-acyl form of ghrelin predominates in circulation (at least 1.8:1 ratio) and might otherwise compete for neutralizing antibodies that do not specifically bind acylated ghrelin over the des-acyl form. The competitive ELISA data in Tables 4A and 4B show that the immunoconjugates comprising the spacer moiety, PEG-Ghr5 in particular, induced high affinity anti-ghrelin antibodies, with a high specificity or preferential affinity for acylated ghrelin. In contrast, hapten 1 (Ghr 1 without the spacer moiety) and hapten 2 (Ghr2 without the spacer moiety) induced high affinity anti-ghrelin antibodies in some instances, but the antibodies generally had no particular selectivity or preferential affinity for the acylated ghrelin over the des-acyl form.

Example 4. Post-Immunization Weight Gain, Food Intake and Feed Efficiency

Mice were immunized as described in Example 2. Body weight and food intake were determined daily (0.1 g precision), 2 h prior to the onset of the dark cycle during the weeks after the fourth and fifth immunizations, by when antibody titers maximized. Feed efficiency was calculated as body weight gained per unit energy intake (mg/kcal). Results are shown in FIG. 5 and Tables 5 and 6.

Figure 5:
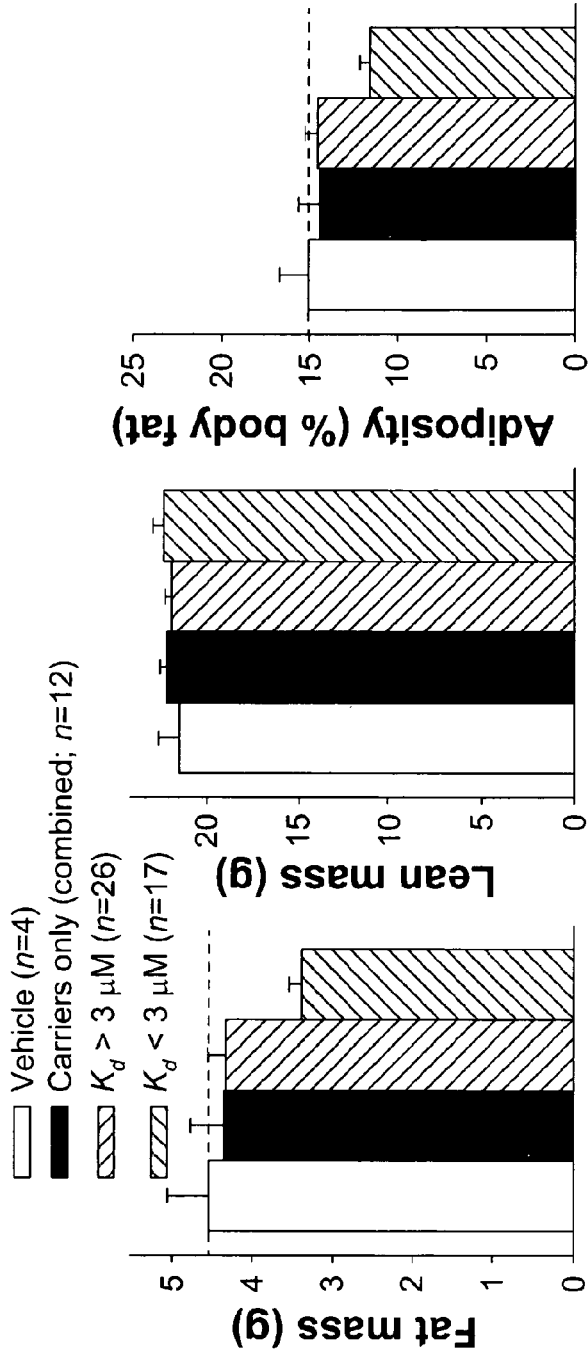
In FIG. 5, 0=carrier only; 1=GSS(butyryl)FLSPEHQC-NH$_2$ (SEQ ID NO:26); 2=CQQRKESKKPPAKLQPR-NH$_2$ (SEQ ID NO:27); 3=GSS(butyryl)FL-PEG$_4$-C—NH$_2$ (SEQ ID NO:31); and 4=GSS(octanoyl)FL-PEG$_4$-C—NH$_2$ (SEQ ID NO:32).

FIG. 5 is a graphical representation of body composition at the 5$^{th}$ bleed in relation to the anti-Ghrelin affinity at the 5$^{th}$ bleed. High anti-ghrelin affinity (<3 μM) at the 5$^{th}$ bleed is associated with lower absolute fat mass and relative fat mass (i.e. adiposity), while sparing lean mass. This threshold of affinity helps predict less subsequent weight gain from the 3$^{rd}$ bleed.

Table 5 shows the result of food deprivation on mice immunized with either the ghrelin hapten immunoconjugates with the carrier proteins tetanus toxin (TT), CRM and keyhole limpet hemocyanin (KLH) or with the carrier protein only. Table 6 shows the weight changes associated with food deprivation and refeeding, where the mice have been immunized with ghrelin hapten immunoconjugates or with carrier proteins alone. Table 7 provides a summary comparison of hapten 2 and 4 immunoconjugates.

TABLE 5

Deprivation-induced 6-hour food intake (g)

| Carrier Protein | Carrier Only | Hapten | |
|---|---|---|---|
| | | 2 | 4 |
| TT | 1.54 + 0.14 | 0.95 + 0.19 | 1.71 + 0.12 |
| CRM | 1.75 + 0.30 | 1.97 + 0.12 | 1.94 + 0.11 |
| KLH | 2.08 + 0.12 | 2.17 + 0.23 | 1.92 + 0.11 |

TABLE 6

Weight change (g) associated with food deprivation/refeeding

| Measure | Carrier Only | Hapten | | | | | |
|---|---|---|---|---|---|---|---|
| | | TT2 | TT4 | CRM2 | CRM4 | KLH2 | KLH4 |
| Deprivation Loss | −0.62 + 0.53 | −3.16 + 1.20 | 0.24 + 1.57 | −2.92 + 1.20 | −1.11 + 2.61 | 0.27 + 0.54 | −3.06 + 0.68 |
| Post-dep Gain | 2.64 + 0.26 | 0.38 + 0.43 | 2.94 + 0.27 | 3.13 + 0.43 | 2.93 + 0.44 | 2.37 + 0.30 | 2.07 + 0.15 |
| Net Change | 2.01 + 0.67 | −2.79 + 1.11 | 2.70 + 1.58 | 0.21 + 1.23 | 1.82 + 2.37 | 2.64 + 0.80 | −0.99 + 0.79 |

TABLE 7

Summary Comparison of Hapten 2 and 4 Immunoconjugates

| | BSA-5 Titer (×100) | Ghrelin affinity (uM, Kd) | Selectivity (des/acyl ratio) | Fat mass (g) | Lean mass (g) | % Fat | % Lean | Ad lib food intake (g) | Deprivation food intake (g) | Greater Deprivation Weight Loss? | Less Regain After Deprivation? |
|---|---|---|---|---|---|---|---|---|---|---|---|
| Vehicle | <2 | ND | ND | 4.54 + 0.52 | 21.41 + 1.17 | 15.1 + 1.6 | 70.9 + 1.4 | ND | ND | | |
| Carrier | ~4 | ND | ND | 4.34 + 0.43 | 22.12 + 0.43 | 14.4 + 1.2 | 74.1 + 1.0 | 4.45 + 0.09 | 1.79 + 0.13 | | |
| TT2 | ~900 | 5.7 | 1 | 3.98 + 0.63 | 21.00 + 1.97 | 14.1 + 1.7 | 75.6 + 1.9 | 4.06 + 0.13 | 0.95 + 0.19 | YES | YES |

TABLE 7-continued

Summary Comparison of Hapten 2 and 4 Immunoconjugates

|  | BSA-5 Titer (×100) | Ghrelin affinity (uM, Kd) | Selectivity (des/acyl ratio) | Fat mass (g) | Lean mass (g) | % Fat | % Lean | Ad lib food intake (g) | Deprivation food intake (g) | Greater Deprivation Weight Loss? | Less Regain After Deprivation? |
|---|---|---|---|---|---|---|---|---|---|---|---|
| CRM2 | ~800 | 2.6 | 1 | 3.29 + 0.11 | 21.07 + 0.27 | 11.4 + 0.3 | 73.0 + 0.3 | 4.00 + 0.11 | 1.97 + 0.12 | YES | NO |
| KLH2 | ~150 | 1.4 | 1 | 3.02 + 0.50 | 25.10 + 1.16 | 9.9 + 1.9 | 81.8 + 1.7 | 4.39 + 0.11 | 2.17 + 0.23 | NO | NO |
| TT4 | ~350 | 0.25 | 22.6 | 3.74 + 0.41 | 22.33 + 1.48 | 13.1 + 1.3 | 78.1 + 1.7 | 4.42 + 0.34 | 1.71 + 0.12 | NO | NO |
| CRM4 | ~1,400 | <0.25 | 53.8 | 3.17 + 0.31 | 21.07 + 1.39 | 11.1 + 1.0 | 74.1 + 1.0 | 4.15 + 0.03 | 1.94 + 0.11 | NO | NO |
| KLH4 | ~350 | 0.25 | 17.5 | 3.55 + 0.25 | 21.77 + 0.98 | 12.5 + 0.9 | 76.3 + 1.8 | 4.18 + 0.21 | 1.92 + 0.11 | YES | YES |

As can be seen from the data in Tables 5 and 6, and the summary data in Table 7, as a whole, mice immunized with ghrelin haptens showed reduced spontaneous food intake during the month following the $5^{th}$ immunization relative to mice immunized with the carrier control. This effect was especially pronounced when CRM was used as the carrier protein, but also seen with TT2 among others.

All groups were at asymptotatic body weight (neutral energy balance) by the time that they reached the month following the $5^{th}$ immunization. Unsurprisingly, then, differences in spontaneous weight gain after the $5^{th}$ immunization were not seen. The TT2 conjugate-treated mice showed reduced food deprivation-induced food intake. Mice which received TT2, CRM2 or KLH4 immunoconjugates showed greater deprivation-induced weight loss and/or less post-deprivation weight gain as compared to other groups.

Example 7. Statistical Analysis

Analyses of variance (ANOVA) were used to identify group differences. Fisher's protected LSD tests were used for posthoc comparisons. Welch's t-tests, corrected for multiple comparisons, were used to compare groups with unequal variance. To reduce heterogeneity of variance and achieve a more normal distribution, data for plasma antibody titers, apparent ghrelin binding affinity constants of plasma, and brain/plasma total ghrelin ratios were first log-transformed for statistical analysis, including calculation of titer selectivity rations. Corresponding values presented in tables or figures represent antilog transformations. Chi-square analysis was used to test whether subjects differed in the frequency of having detectable circulating cytokine levels. The software package was Systat 11.0 (SPSS, Chicago Ill., USA).

Further studies were performed to examine activities of antibodies generated with the ghrelin hapten immunoconjugates of the invention. It was found that monoclonal antibodies elicited with ghrelin hapten-KLH conjugates bind with high specificity to ghrelin. In addition, oligoclonal anti-ghrelin antibodies thus generated were shown to be able to increases energy expenditure and reduces food intake in fasted mice. See, Zakhari et al., Mol. Pharm. 2011 Dec. 23. These studies further demonstrated the utilities of the ghrelin haptens and related immunoconjugates of the invention in effective anti-ghrelin immunoneutralization and in ghrelin immunopharmacotherapy on whole body metabolism and food intake in vivo.

The invention thus has been disclosed broadly and illustrated in reference to representative embodiments described above. It is understood that various modifications can be made to the present invention without departing from the spirit and scope thereof. It is further noted that all publications, patents and patent applications cited herein are hereby expressly incorporated by reference in their entirety and for all purposes as if each is individually so denoted. Definitions that are contained in text incorporated by reference are excluded to the extent that they contradict definitions in this disclosure.

We claim:

1. An immunoconjugate comprising the following structure:

Gly-Ser-A-Phe-Leu-B-C-F;

Gly-Ser-A-Phe-Leu-B-C-D-F; or

Gly-Ser-A-Phe-Leu-B-C-D-E-F;

wherein

A comprises:

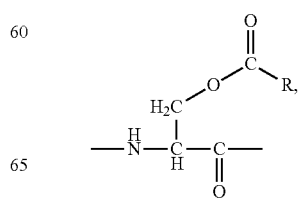

wherein R is selected from the group consisting of $C_{3-10}$ alkyl, $C_{4-8}$ cycloalkyl, and $C_{5-8}$ aryl;

B comprises a subsequence of 0 to 23 consecutive amino acids of SEQ ID NO: 1;

C comprises a spacer moiety comprising 1 to about 5 consecutive PEG amino acid spacers (p) containing 1 to about 40 polyethylene glycol (PEG) units:

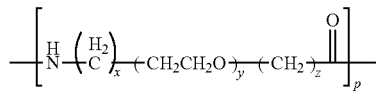

wherein x is between 1 and 2 inclusive, y is between 1 and 40 inclusive, z is between 0 and 2 inclusive, p is between 1 and 5 inclusive;

D comprises a conjugation moiety with a chemical functionality suitable for conjugation with the linker moiety or directly with a carrier protein;

E comprises a linker moiety with chemical functionality suitable for conjugation with the conjugation moiety; and F comprises a protein carrier moiety.

2. The immunoconjugate of claim 1, wherein R comprises $CH_2CH_2CH_3$ or $CH_2CH_2CH_2CH_2CH_2CH_2CH_3$.

3. The immunoconjugate of claim 1, wherein B comprises 0 residues of SEQ ID NO: 1.

4. The immunoconjugate of claim 1, wherein the PEG units are linear, branched, or multiply branched.

5. The immunoconjugate of claim 1, wherein y is between 1 to about 30 inclusive.

6. The immunoconjugate of claim 1, wherein y comprises between 1 to about 8 inclusive.

7. The immunoconjugate of claim 1, wherein C comprises one PEG amino acid spacer containing four PEG units, wherein x=1, y=4, z=1 and p=1.

8. The immunoconjugate of claim 1, wherein D comprises a Lys, Cys, His, Arg, Asp, Glut, Ser, Thr, or Tyr residue.

9. The immunoconjugate of claim 8, wherein D is a Cys residue.

10. The immunoconjugate of claim 1, wherein E comprises a N-maelimidoalkylcarboxyl moiety.

11. The immunoconjugate of claim 10, where E comprises a N-γ-maleimidobutyryl (GMB) linker.

12. The immunoconjugate of claim 1, wherein the protein carrier moiety F comprises serum albumin, keyhole limpet hemocyanin (KLH), thyroglobulin, ovalbumin, bovine serum albumin (BSA), tetanus toxoid (TT), or diphtheria toxoid (CRM).

13. The immunoconjugate of claim 1, wherein
R comprises $CH_2CH_2CH_3$;
B comprises 0 residues of SEQ ID NO: 1;
C comprises one PEG amino acid spacer containing four PEG units, wherein x=1, y=4, z=1 and p=1;
D is a Cys residue; and
E is a N-γ-maleimidobutyryl (GMB) linker.

14. The immunoconjugate of claim 1, wherein
R comprises $CH_2CH_2CH_2CH_2CH_2CH_2CH_3$;
B comprises 0 residues of SEQ ID NO: 1;
C comprises one PEG amino acid spacer containing four PEG units, wherein x=1, y=4, z=1 and p=1;
D is a Cys residue; and
E is N-γ-maleimidobutyryl (GMB) linker.

15. An immunogenic composition comprising an immunoconjugate of any one of claims 1 to 14 and a physiologically acceptable vehicle.

16. The immunogenic composition of claim 15, wherein the immunogenic composition comprises a vaccine.

17. A method of decreasing adiposity in a subject, comprising administering to the subject an immunogenic composition of claim 15 or claim 16.

18. A method of inhibiting weight gain by a subject, comprising administering to the subject an immunogenic composition of claim 15 or claim 16.

19. A method of inhibiting the development of obesity in a subject, comprising administering to the subject an immunogenic composition of claim 15 or claim 16.

20. A method of sparing lean body mass in a subject during low-calorie diet-induced weight loss, comprising administering to the subject an immunogenic composition of claim 15 or claim 16.

21. The method of any one of claims 17-19 or 20, wherein the subject is human.

* * * * *